(12) United States Patent
Kreek et al.

(10) Patent No.: US 6,337,207 B1
(45) Date of Patent: Jan. 8, 2002

(54) ALLELES OF THE HUMAN MU OPIOID RECEPTOR, DIAGNOSTIC METHODS USING SAID ALLELES, AND METHODS OF TREATMENT BASED THEREON

(75) Inventors: Mary Jeanne Kreek; Karl Steven LaForge, both of New York, NY (US); Lei Yu, Cincinnati, OH (US); Jay A. Tischfield, Carmel, IN (US)

(73) Assignees: The Rockefeller University, New York, NY (US); The Advanced Research and Technology Institute, Inc., Bloomington, IN (US)

( * ) Notice: Subject to any disclaimer, the term of this patent is extended or adjusted under 35 U.S.C. 154(b) by 0 days.

(21) Appl. No.: 09/113,426

(22) Filed: Jul. 10, 1998

(51) Int. Cl.$^7$ .................. C12N 15/63; C12N 15/85; C07H 21/04
(52) U.S. Cl. ............... 435/320.1; 536/23.5; 435/325
(58) Field of Search ................ 536/23.5, 24.33; 435/91.2, 6, 325, 320.1, 252.3

(56) References Cited

U.S. PATENT DOCUMENTS 4,800,159 A * 1/1989 Mullis et al. ............ 435/172.3

FOREIGN PATENT DOCUMENTS

WO  9520667  *  3/1995

OTHER PUBLICATIONS

Bergen et al. (1997) Molecular Psychiatry 2: 490–494.*

* cited by examiner

*Primary Examiner*—Lisa B. Arthur
(74) *Attorney, Agent, or Firm*—Klauber & Jackson

(57) ABSTRACT

Provided herein are variant alleles of a gene encoding a mu opioid receptor, along with cloning vectors for replicating such variant alleles, expressing vectors for expressing the variant alleles to produce variant mu opioid receptors, and antibodies to such variant receptors. Also disclosed are binding characteristics of such variant receptors regarding binding to opioid ligands, and the using of such binding characteristics to diagnose a subjects susceptibility to pain, susceptibility to an addictive disease, selecting an appropriate pain reliever along with a therapeutically effective amount of the reliever to administer to a subject suffering from pain. In addition, diagnostic methods for diagnosing a disease or disorder such as infertility, constipation, diarrhea, decreased immune response relative to a standard, and decreased ability to withstand stress relative to a standard, along with commercial kits for diagnosing such diseases or disorders.

21 Claims, 6 Drawing Sheets

FIG.4A

```
   1 ggaattccgg ctataggcag aggagaatgt cagatgctca gctcggtccc ctccgcctga
  61 cgctccctc tgtctcagcc aggactggtt tctgtaagaa acagcaggag ctgtggcagc
 121 ggcgaaagga agcggctgag gcgcttggaa cccgaaaagt ctcggtgctc ctggctacct
 181 cgcacagcgg tgcccgcccg gccgtcagta ccatggacag cagcgctgcc cccacgaacg
 241 ccagcaattg cactgatgcc ttggcgtact caagttgctc cccagcaccc agccccgtt
 301 cctggtcaa cttgtcccac ttagatggca acctgtccga cccatgcggt ccgaaccgca
 361 ccaacctggg cgggagagac agcctgtgcc ctccgaccgg cagtccctcc atgatcacgg
 421 ccatcacgat catgccctc tactccatcg tgtgcgtggt gggctcttc ggaaacttcc
 481 tggtcatgta tgtgattgtc agatacacca agatgaagac tgccaccaac atctacattt
 541 tcaaccttgc tctggcagat gccttagcca ccagtaccct gcccttccag agtgtgaatt
 601 acctaatggg aacatggcca tttggaaacca tcctttgcaa gatagtgatc tccatagatt
 661 actataacat gttcaccagc atattcaccc tctgcaccat gagtgttgat cgatacattg
 721 cagtctgcca ccctgtcaag gcctagatt tccgtactcc ccgaaatgcc aaaattatca
 781 atgtctgcaa ctggatcctc tcttcagcca ttgttcttcc tgtaatgttc atggctacaa
 841 caaatacag gcaaggttcc atagattgta ctaacatt ctctcatcca acctggtact
 901 gggaaaacct cgtgaagatc tgtgttttca tgatcttgc gcctcaagag gtgctcatca
 961 ttaccgtgtg ctatgactg atgcaggaat cttcgaagga tcaccaggat tcaccaggat gtcccgcatg tgtccgcatg ctctctgct
1021 ccaagaaaa ggacaggaat cttcgaagga tcaccaggaa tcaccaggaa tcaccaggaa ggtgctggtg gtggtggctg
1081 tgttcatcgt ctgctggact ccattcatt cccattcaca tttacgtcat cattaaagcc ttggttacaa
```

FIG.4B

```
1141  tcccagaaac  tacgttccag  actgtttctt  ggcacttctg  cattgctcta  ggttacacaa
1201  acagctgcct  caacccagtc  ctttatgcat  ttctggatga  aaacttcaaa  cgatgcttca
1261  gagagttctg  tatcccaacc  tcttccaaca  ttgagcaaca  aaactccact  cgaattcgtc
1321  agaacactag  agaccacccc  tccacggcca  atacagtgga  tagaactaat  catcagctag
1381  aaaatctgga  agcagaaact  gctccgttgc  cctaacaggg  tctcatgcca  ttccgacctt
1441  caccaagctt  agaagccacc  atgtatgtacc  aagcaggttg  cttcaagaat  gtgtaggagg
1501  ctctaattct  ctaggaaagt  gcctactttt  aggtcatcca  acctctttcc  tctctgcca
1561  ctctgctctg  cacattagag  ggacagccaa  aagtaagtgg  agcatttgga  aggaaaggaa
1621  tatacacac   cgaggagtcc  agtttgtgca  agacacccag  tggaaccaaa  accatcgtg
1681  gtatgtgaat  tgaagtcatc  ataaaaggtg  acccttctgt  ctgtaagatt  ttattttcaa
1741  gcaaatattt  atgacctcaa  caaagaagaa  accctttttg  ttaagttcac  cgtagtaaca
1801  cataaagtaa  atgctacctc  tgatcaaagc  accttgaatg  gaaggtccga  gtctttttag
1861  tgttttttgca agggaatgaa  tccattattc  tatttttagac tttaacttc  aacttaaaat
1921  tagcatctgg  ctaaggcatc  atttttcacct  ccattctctg  gttttgtatt  gtttaaaaaa
1981  aataacatct  ctttcatcta  gctccataat  tgcaagggaa  gagattagca  tgaaaggtaa
2041  tctgaaacac  agtcatgtgt  canctgtaga  aaggttgatt  ctcatgcact  ncaaatactt
2101  ccaaagagtc  atcatggggg  atttttcatt  cttaggcttt  cagtggtttg  ttcctgaat
2161  tc
```

FIG. 5

```
             1          *          *                      *50
hMOR1   MDSSAAPTNA  SNCTDALAYS  SCSPAPSPGS  WVNLSHLDGN  LSDPCGPNRT
rMOR1   MDSSTGPGNT  SDCSDPLAQA  SCSPA..PGS  WLNLSHVDGN  QSDPCGLNRT
rDOR1   ..........  ..........  .MEPVPSARA  ELQFSLL.AN  VSDTFPSAFP
rKOR1   ........ME  SPIQIFRGEP  GPTCAPSACL  LPN.......  .SSSWFPNWA 51                                               100
hMOR1   NLGGRDSLCP  P....TGSP.  SMITAITIMA  LYSIVCVVGL  FGNFLVMYVI
rMOR1   GLGGNDSLCP  Q....TGSP.  SMITAITIMA  LYSIVCVVGL  FGNFLVMYVI
rDOR1   SASANASGSP  G....ARSAS  SLALAIAITA  LYSAVCAVGL  LGNVLVMFGI
rKOR1   ESDSNGSVGS  EDQQLEPAHI  SPAIPVIITA  VYSVVFVVGL  VGNSLVMFVI 101                                              150
hMOR1   VRYTKMKTAT  NIYIFNLALA  DALATSTLPF  QSVNYLMGTW  PFGTILCKIV
rMOR1   VRYTKMKTAT  NIYIFNLALA  DALATSTLPF  QSVNYLMGTW  PFGTILCKIV
rDOR1   VRYTKLKTAT  NIYIFNLALA  DALATSTLPF  QSAKYLMETW  PFGELLCKAV
rKOR1   IRYTKMKTAT  NIYIFNLALA  DALVTTTMPF  QSAVYLMNSW  PFGDVLCKIV 151                                              200
hMOR1   ISIDYYNMFT  SIFTLCTMSV  DRYIAVCHPV  KALDFRTPRN  AKIINVCNWI
rMOR1   ISIDYYNMFT  SIFTLCTMSV  DRYIAVCHPV  KALDFRTPRN  AKIVNVCNWI
rDOR1   LSIDYYNMFT  SIFTLTMMSV  DRYIAVCHPV  KALDFRTPAK  AKLINICIWV
rKOR1   ISIDYYNMFT  SIFTLTMMSV  DRYIAVCHPV  KALDFRTPLK  AKIINICIWL

201                     @                        250
hMOR1   LSSAIGLPVM  FMATTKYRQ.  .GSIDCTLTF  SHPTW.YWEN  LLKICVFIFA
rMOR1   LSSAIGLPVM  FMATTKYRQ.  .GSIDCTLTF  SHPTW.YWEN  LLKICVFIFA
rDOR1   LASGVGVPIM  VMAVTQPRD.  .GAVVCTLQF  PSPSW.YWDT  VTKICVFLFA
rKOR1   LASSVGISAI  VLGGTKVRED  VDVIECSLQF  PDDEYSWWDL  FMKICVFVFA 251                                              300
hMOR1   FIMPVLIITV  CYGLMILRLK  SVRMLSGSKE  KDRNLRRITR  MVLVVVAVFI
rMOR1   FIMPVLIITV  CYGLMILRLK  SVRMLSGSKE  KDRNLRRITR  MVLVVVAVFI
rDOR1   FVVPILIITV  CYGLMLLRLR  SVRLLSGSKE  KDRNLRRITR  MVLVVVGAFV
rKOR1   FVIPVLIIIV  CYTLMILRLK  SVRLLSGSRE  KDRNLRRITK  LVLVVVAVFI 301                                              350
hMOR1   VCWTPIHIYV  IIKALVTI.P  ETTFQTVSWH  FCIALGYTNS  CLNPVLYAFL
rMOR1   VCWTPIHIYV  IIKALITI.P  ETTFQTVSWH  FCIALGYTNS  CLNPVLYAFL
rDOR1   VCWAPIHIFV  IVWTLVDINR  RDPLVVAALH  LCIALGYANS  SLNPVLYAFL
rKOR1   ICWTPIHIFI  LVEALGSTSH  STAVLS.SYY  FCIALGYTNS  SLNPVLYAFL

351                                          @400
hMOR1   DENFKRCFRE  FCIPTSSNIE  QQNSTRIRQN  TRDHPSTANT  VDRTNHQLEN
rMOR1   DENFKRCFRE  FCIPTSSTIE  QQNSTRVRQN  TREHPSTANT  VDRTNHQLEN
rDOR1   DENFKRCFRQ  LCRAPCGGQE  PGSLRRPRQA  TARERVTACT  PS......DG
rKOR1   DENFKRCFRD  FCFPIKMRME  RQSTNRVR.N  TVQDPASMRD  VGGMNKPV 401
hMOR1   LEAETAPLP
rMOR1   LEAETAPLP
rDOR1   PGGGAAA
```

ALLELES OF THE HUMAN MU OPIOID RECEPTOR, DIAGNOSTIC METHODS USING SAID ALLELES, AND METHODS OF TREATMENT BASED THEREON

GOVERNMENTAL SUPPORT

This invention was made government support under Grant Nos. NIDA R01-DA09444, NIDA P50-DA05130, and NIDA K05-DA00049 awarded by the National Institute of Drug Addiction. The Government has certain rights in the invention.

FIELD OF THE INVENTION

This invention relates generally to alleles of the human mu opioid receptor gene, along with products derived from such alleles. Also included herein are methods of diagnosing various susceptibilities using such alleles and determining treatment for certain diseases based upon the presence of specific alleles of the human mu opioid receptor gene, and various diseases or disorders related to physiological functions regulated by the hypothalamus pituitary adrenal axis (HPA) or the hypothalamus pituitary gonadal axis (HPG).

BACKGROUND OF THE INVENTION

Opioid drugs have various effects on perception of pain, consciousness, motor control, mood, autonomic function, and can also induce physical dependence. The endogenous opioid system plays an important role in modulating endocrine, cardiovascular, respiratory, gastrointestinal functions, and immune functions. Opioids, either exogenous or endogenous, exert their actions by binding to specific membrane-associated receptors.

Examples of exogenous opioids presently known include, opium, heroin, morphine, codeine, fentanyl, and methadone, to name only a few. Moreover, a family of over 20 endogenous opioid peptides has been identified, wherein the members possess common structural features, including a positive charge juxtaposed with an aromatic ring that is required for interaction with an opioid receptor. It has been determined that most, if not all the endogenous opioid peptides are derived from the proteolytic processing of three precursor proteins, i.e., pro-opiomelanocortin, proenkephalin, and prodynorphin. In addition, a fourth class of endogenous opioids, the endorphins, has been identified (the gene encoding these proteins has not yet been cloned). In the processing of the endogenous opioid precursor proteins, initial cleavages are made by membrane-bound proteases that cut next to pairs of positively charged amino acid residues, and then trimming reactions produce the final endogenous opioids secreted from cells in vivo. Different cell types contain different processing enzymes so that, for example proopiomelanocortin can be processed into different endogenous peptides by different cells. For example, in the anterior lobe of the pituitary gland, only corticotropin (ACTH), β-lipotropin, and β-endorphin are produced. Both pro-enkephalin and pro-dynorphin are similarly processed by specific enzymes in specific cells to yield multiple opioid peptides.

Pharmacological studies have suggested there are numerous classes of opioid receptors which bind to exogenous and endogenous opioids. These classes differ in their affinity for various opioid ligands and in their cellular and organ distribution. Moreover, although the different classes are believed to serve different physiological functions, there is substantial overlap of function, as well as of distribution.

In particular, there are at least three known types of opioid receptors, mu ($\mu$), delta ($\delta$), and kappa ($\kappa$), to which morphine, the enkephalins, and the dynorphins can bind. These three opioid receptor types are the sites of action of opioid ligands producing analgesic effects. However, the type of pain inhibited and the secondary functions vary with each receptor type. The mu receptor is generally regarded as primarily associated with pain relief, and drug or other chemical dependence, ie. addiction and alcoholism.

The human mu opioid receptor, which modulates corticotropin releasing hormone, has been isolated and described in PCT Application WO 95/07983 (Mar. 23, 1995) (SEQ ID NO:1) as well as in Chen, Y., Mestek, A., Hurley, J. A., & Yu, L. (1993) Mol. Pharmacol. 44, 8–12, and Wang, et al., FEBS letters, (1994)338:217–222. Furthermore, SEQ ID NO:1 can readily be obtained in GENBANK under accession number L25119. The cDNA therefore contains an open reading frame capable of encoding a protein of 400 amino acid residues with 94% sequence similarity to the rat mu opioid receptor. Hydropathy analysis of the deduced protein indicates the presence of seven hydrophobic domains, typical of G-protein-coupled receptors. The N-terminus contains five potential N-linked glycosylation sites which remain conserved between the human and the rat mu opioid receptor.

In the body and brain, heroin is hydrolyzed to morphine, which acts at the mu opioid receptor and results in an euphoric effect and confers the reinforcing properties of the drug and contributes to development of addiction. Heroin addiction can be managed through treatment, primarily methadone maintenance. However, the biological basis of heroin addiction may include diversity of gene structure. Such genetic diversity of the human mu opioid receptor, and the impact of such diversity on receptor function, could contribute to the success or failure of pharmacological management. Similar problems with respect to patient response to pharmacological treatment could occur in most, if not all addictive diseases, such as heroin addiction, alcohol addiction, or cocaine addiction to name only a few, or a combination thereof.

Moreover, addiction to opioid drugs, especially heroin, is a major social problem in the United States, and throughout the world. For example, recent epidemiological assessments sponsored by the NIH-NIDA and other federal agencies have found that around 2.7 million persons in the United States have used heroin at some time. Moreover, the numbers of "hardcore" long-term heroin addicts (addiction being defined herein as self administration of a regular, multiple, daily dose use of a short-acting opioid, such as heroin, for one year or more, with the development of tolerance, physical dependence and drug-seeking behavior, a definition codified in the Federal guidelines governing pharmacotherapy using long-acting agents such as methadone or LAAM, and used as the minimal requirement for entry into treatment) are now estimated to be approximately one million persons. In addition, it has been estimated that around 24 million persons in the United States have used cocaine for some time, and of that number, approximately one million use cocaine regularly, and at least 600,000–700,000 are cocaine addicts.

In view of the importance of the human mu opioid receptor in the study of addiction, and the epidemic proportions of drug addiction, especially to heroin, alcohol or cocaine, or a combination thereof, in the United States and throughout the world, and its involvement in the neuroendocrine system, and physiological functions regulated thereby, efforts have been made to investigate whether any polymorphisms in the gene encoding the human mu opioid receptor exist in the population, and whether such polymorphisms result in a phenotype that has an increased or decreased susceptibility towards development of addiction to exogenous opioids, such as heroin, or alcohol, cocaine, or other addictive drugs. For example, in an article entitled Human mu opioid receptor gene polymorphisms and vulnerability to substance abuse (Berrettini, W. H., Hoehe, M. R., Ferraro, T. N., DeMaria, P. A., and Gottheil, E., *Addiction Biology* 2:303–308 (1997)), two polymorphisms in the human mu opioid receptor gene were reported. One polymorphism (G to T) occurs at nucleotide 175 preceding initiation of translation, and a second coding polymorphism (C to T) at nucleotide 229 (with respect to transcription initiation) on exon I results in an Ala to Val residue change. However, data taken from a study indicated the C229T polymorphism does not differ in occurrence with statistical significance in addicts relative to non addicts (Id at 306). No functional studies were reported.

It has been further determined that a receptor for both endogenous and exogenous opioids modulates the activity of the hypothalamus pituitary adrenal axis (HPA) and the hypothalamus pituitary gonadal axis (HPG), which effects the neuroendocrine system and its production of signaling compounds that play important roles in regulation of numerous physiological functions. In particular, the neuroendocrine system involves the integration of the neural and endocrine systems of the body, and is responsible for the coordination of numerous bodily functions. An important part of this system is the hypothalamus, a specialized portion of the brain involved in receiving and relaying messages from the central nervous system to other parts of the body. Upon stimulation by chemical signals from the central nervous system, the hypothalamus secretes hypothalamic hormones, such as corticotropin releasing factor (CRF) or hormone and gonadotropin releasing hormone or luteinizing hormone releasing hormone. These factors in turn stimulate the anterior pituitary gland to secrete tropic hormones, or tropins, which are synthesized as relatively long polypeptides, and then are then biotransformed to produce active peptide hormones. Pro-opiomelanocortin, which is processed into several active peptide hormones, including adrenocorticotropic hormone (ACTH), is an example of a tropic hormone. ACTH stimulates the adrenal cortex to secrete additional hormones, like cortisol, a stress hormone in humans which regulates glucose metabolism, and targets many tissues in the body. In addition, examples of hormones produced by the anterior pituitary glad upon stimulation with gonadotropin releasing hormone include follicle-stimulating hormone and luteinizing hormones. These hormones stimulate the gonads, such as the ovaries and the testes, to secrete androgens, such as testosterone, progesterone, and estrogen, which in turn affect sexual development, sexual behavior, and other reproductive and nonreproductive functions. As a result, the endogenous opioid system plays an important role in modulating endocrine, reproductive, cardiovascular, respiratory, gastrointestinal, immune functions, sexual development and function, as well as a person's response to stress.

More specifically, in humans, it has been determined that chronic administration of opioids has an inhibitory effect on the HPA axis [McDonald et al., Effect of morphine and nalorhine on plasma hydrocortisone levels in man. J. Pharmacol. Exp. Ther. 125:241247 (1959)]. Basal levels of ACTH and cortisol are significantly disrupted in active heroin addicts: suppression of ACTH and cortisol and abnormal diurnal rhythms of these hormones are found [Kreek, Medical safety and side effects of methadone in tolerant individuals. JAMA 223:665–668 (1973)]. Basal levels and the diurnal rhythm of ACTH and cortisol, which are disrupted in active heroin addicts, have been shown to become normalized in moderate to high dose, long-term methadone-maintained patients when compared to those of healthy volunteer subjects [Kreek, 1973; Kreek et al., Circadian rhythms and levels of beta-endorphin, ACTH, and cortisol during chronic methadone maintenance treatment in humans. Life Sci. 33:409–411 (1983); Kreek et al., Prolonged (24 hour) infusion of the opioid antagonist naloxone does not significantly alter plasma levels of cortisol and ACTH in humans. Proceedings of the 7th International Congress on Endocrinology Elsevier Science p1170, 1984].

In healthy volunteers, ACTH and cortisol levels decrease below the basal levels in response to the infusion of β-endorphin indicating feedback of inhibition of pituitary ACTH release or suppression of hypothalamic CRF release by β-endorphin [Taylor, et al., Beta-endorphin suppresses adrenocroticotropin and cortisol levels in normal human subjects. J. Clin. Endocrinol. Metab. 57:592–596 (1983)], and also naloxone (an opioid antagonist) stimulates a rise in serum ACTH and cortisol, suggesting that the HPA axis is under the tonic inhibitory control of endogenous opioids normalized in steady-state chronic methadone-maintained patients; their HPA axis responses to metyrapone-induced stress appear to be no different from that of healthy volunteer subjects [Kreek, 1973; Kreek et al., Prolonged (24 hour) infusion of the opioid antagonist naloxone does not significantly alter plasma levels of cortisol and ACTH in humans. Proceedings of the 7th International Congress on Endocrinology Elsevier Science p1170, 1984].

Support for the effects of opioids on physiological functions regulated by the HPA and the HPG axes can be found in observations of heroin addicts. More specifically, it has been observed that many heroin addicts are infertile, and in the case of female addicts, their menstrual cycle is dramatically disrupted to the point that they do not ovulate. Furthermore, it has been observed that heroin addicts, and nonaddicted patients taking morphine, become constipated, and that the immune systems of addicts is weakened relative to the immune system of non addicts. However, once therapeutic agents designed to treat addiction, such as methadone, addicts become fertile, are no longer constipated, and have a immune system whose ability to fight foreign bodies is in parity with the immune system of a nonaddict.

Hence, what is needed is discovery of heretofore unknown polymorphisms of the human mu opioid receptor gene that can be used as genetic markers to map the locus of the human mu opioid receptor gene in the genome.

What is also needed are the DNA sequences of heretofore unknown isolated nucleic acid molecules which encode human mu opioid receptors, wherein the DNA sequences include a combination of presently known and subsequently discovered polymorphisms of the human mu opioid receptors.

Furthermore, what is needed is the characterization of the binding properties of heretofore unknown human mu opioid receptors produced from the expression of genes comprising such heretofore unknown polymorphisms of the human mu opioid receptor gene, or combinations of unknown polymorphisms and known polymorphisms.

Furthermore, what is needed is a characterization of the activity of such unknown human mu opioid receptors produced from the expression of nucleic acid molecules comprising such polymorphisms.

What is also needed is a correlation between polymorphisms of the human mu opioid receptor gene, and the susceptibility of a subject to addictive diseases, such as heroin addiction, cocaine addiction, or alcohol addiction, to name only a few.

What is also needed are diagnostic methods to determine a subject's increased or decreased susceptibility to addictive diseases. With the results of such methods, targeted prevention methods, early therapeutic intervention, and improved chronic treatment to opioid addiction can be developed. Physicians armed with the results of such diagnostic methods can determine whether administration to a subject of opioid analgesics is appropriate or whether non-opioid derived analgesics should be administered to the subject. Also, appropriate choice and type of analgesic can be made in treating a subject's pain.

What is also need are methods of determining a subject's susceptibility to pain and responsibility to analgesics, and using that information when prescribing analgesics to the subject. What is also needed is an ability to determine the binding affinity of the mu opioid receptor to endogenous opioids, such as β-endorphin, and the effect of this binding activity on the neuroendocrine system.

The citation of any reference herein should not be construed as an admission that such reference is available as "Prior Art" to the instant application.

SUMMARY OF THE INVENTION

There is provided, in accordance with the present invention, heretofore unknown polymorphisms of the human mu opioid receptor gene, and their use in mapping the locus of the human mu opioid receptor gene, determining susceptibility to addictive diseases, determining susceptibility to pain, and determining a therapeutically effective amount of pain reliever to administer to a subject suffering from pain, diagnosing a disease or disorder in a subject that is related to a physiological function regulated by the HPA or HPG axes of the neuroendocrine system, and selecting an appropriate therapeutic agent and a therapeutically effective amount of such an agent to administer to a subject suffering from a disease or disorder related to a physiological function regulated by the HPA or HPG.

Hence, the present invention extends to heretofore unknown polymorphisms of the human mu opioid receptor gene that can serve as genetic markers to map the locus of the human mu opioid receptor gene.

The present invention further extends to DNA sequences of heretofore unknown isolated nucleic acid molecules which encode human mu opioid receptors, wherein the DNA sequences include a combination of presently known polymorphisms and polymorphisms of the human mu opioid receptors discovered by Applicants.

The present invention further extends to the characterization of the binding properties of heretofore unknown human mu opioid receptors produced from the expression of isolated nucleic acid molecules comprising DNA sequences with such heretofore unknown polymorphisms of the human mu opioid receptor gene, or combinations of unknown polymorphisms and known polymorphisms.

Furthermore, the present invention extends to characterizing the activity of such unknown human mu opioid receptors and particularly the increased or decreased ability of mu opioid receptors produced from isolated nucleic acid acids of the present invention to activate G protein-activated inwardly rectifying K$^+$ (GIRK) channels via a G protein-mediated mechanism.

The present invention further extends to Applicants' discovery that polymorphisms in an allele comprising a DNA sequence of SEQ ID NO:1, such as A118G and C17T, which are described in further detail infra, are present in the population at a high frequency (greater than5%).

Furthermore, the present invention extends to Applicant's discovery of a correlation between polymorphisms of the human mu opioid receptor gene, and the increased or decreased susceptibility of a subject to addictive diseases, such as heroin addiction, cocaine addiction, or alcohol addiction, to name only a few.

The present invention further extends to diagnostic methods to determine a subject's increased or decreased susceptibility to addictive diseases. With the results of such methods, targeted prevention methods, early therapeutic intervention, and improved chronic treatment to opioid addiction are set forth herein and encompassed by the present invention. In addition, attending medical professionals armed with the results of such diagnostic methods can determine whether administration of opioid analgesics is appropriate or whether non-opioid derived analgesics should be administered to the subject. Furthermore, appropriate choice and type of analgesic to treat a subject's pain can be made.

Also, the present invention extends to methods of determining a subject's increased or decreased susceptibility to pain and response to analgesics, and the use of the information in prescribing analgesics to the subject.

In addition, the present invention extends to methods of diagnosing a disease or disorder in a subject, wherein the disease or disorder is related to a physiological function regulated by the HPA or HPG axes of the neuroendocrine system. Examples of such physiological functions include reproductive or sexual functions, gastrointestinal motility, immune response, and ability to withstand stress.

Broadly the present invention extends to an isolated variant allele of a human mu opioid receptor gene which can serve as a genetic marker, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises:

G24A;

G779A; or

G942A, or combinations thereof.

Furthermore, the present invention extends to an isolated variant allele of a human mu opioid receptor gene as set forth above, which is detectably labeled. Numerous detectable labels have applications in the present invention, such as radioactive elements, chemicals which fluoresces, or enzymes, to name only a few.

The present invention further extends to an isolated nucleic acid molecule hybridizable under standard hybridization conditions to an isolated variant allele of the human mu opioid receptor gene, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises:

G24A;

G779A; or

G942A, or combinations thereof.

Moreover, the present invention extends to an isolated nucleic acid molecule hybridizable under standard hybridization conditions to an isolated variant allele of the human mu opioid receptor gene, wherein the predominant or "most common" allele of a human mu opioid receptor gene found in the population comprises a DNA sequence of SEQ ID NO:1, and a variant allele of the present invention comprises a DNA sequence having a variation in SEQ ID NO: 1, wherein the variation comprises:

G24A;

G779A; or

G942A, or combinations thereof, wherein the isolated nucleic acid molecule is detectably labeled. Examples of detectable labels that have applications in this embodiment of the present invention are described above.

In addition, the present invention extends to an isolated variant allele of a human mu opioid receptor gene, wherein the predominant or "most common" allele of the human mu opioid receptor gene encodes a human mu opioid receptor comprising an amino acid sequence of SEQ ID NO:2, and the variant allele of the human mu opioid receptor gene encodes a variant human mu opioid receptor comprising an amino acid sequence having a variation in SEQ ID NO:2, wherein the variation comprises Arg260His.

Furthermore, the present invention extends to an isolated nucleic acid molecule hybridizable under standard hybridization conditions to an isolated variant allele of a human mu opioid receptor gene of the present invention, wherein the isolated nucleic acid molecule encodes a variant human mu opioid receptor comprising an amino acid sequence having a variation in SEQ ID NO:2, wherein the variation comprises Arg260His.

Naturally, the present invention extends to a variant human mu opioid receptor comprising an amino acid sequence having a variation in SEQ ID NO:2, wherein the variation comprises Arg260His.

Furthermore, the present invention extends to an antibody having a variant human mu opioid receptor comprising an amino acid sequence having a variation in SEQ ID NO:2, wherein the variation comprises Arg260His as an immunogen. Such an antibody can be a polyclonal antibody, a monoclonal antibody, or a chimeric antibody. Moreover, an antibody of the present invention can be detectably labeled. Examples of detectable labels which have applications in this embodiment comprises a radioactive element, a chemical which fluoresces, or an enzyme, to name only a few.

In addition, the present invention extends to cloning vectors that can be used to clone copies of a variant alleles of a human mu opioid receptor gene of the present invention. For example, the present invention extends to a cloning vector comprising an isolated variant allele of a human mu opioid receptor gene and an origin of replication, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises:

G24A;

G779A; or

G942A, or combinations thereof.

In another embodiment, the present invention extends to a cloning vector comprising an isolated nucleic acid molecule hybridizable under standard hybridization conditions to an isolated variant allele of a human mu opioid receptor gene, and an origin of replication, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises:

G24A;

G779A; or

G942A, or combinations thereof.

Numerous cloning vectors have applications in the present invention. For example, a cloning vector having applications in the present invention includes *E. coli*, bacteriophages such as lambda derivatives, plasmids such as pBR322 derivatives, and pUC plasmid derivatives such as pGEX vectors or pmal-c or pFLAG, to name only a few.

Naturally, the present invention extends to expression vectors comprising an isolated variant allele a human mu opioid receptor gene operatively associated with a promoter, wherein the predominant or "most common" allele of a human mu opioid receptor gene found in the population comprises a DNA sequence of SEQ ID NO: 1, and a variant allele of the present invention comprises a DNA sequence having a variation in SEQ ID NO:1, wherein the variation comprises:

G24A;

G779A; or

G942A, or combinations thereof.

Furthermore, the present invention extends to an expression vector comprising an isolated nucleic acid molecule hybridizable under standard hybridization conditions to an isolated variant allele a human mu opioid receptor gene, wherein the isolated nucleic acid molecule is operatively associated with a promoter. As set forth above, the predominant or "most common" allele of a human mu opioid receptor gene found in the population comprises a DNA sequence of SEQ ID NO:1, and a variant allele of the present invention comprises a DNA sequence having a variation in SEQ ID NO: 1, wherein the variation comprises:

G24A;

G779A; or

G942A, or combinations thereof.

Numerous promoters have applications in an expression vector of the present invention, including but not limited to immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor, to name only a few.

In addition, the present invention extends to a unicellular host transformed or transfected with an expression vector of the present invention. Examples of hosts which can be transformed or transfected with an expression vector of the present invention, and have applications in the present invention, include, but are not limited to, *E. coli*, Pseudonomas, Bacillus, Strepomyces, yeast, CHO, R1.1, B-W, L-M, COS1, COS7, BSC1, BSC40, BMT10 or Sf9 cells.

Naturally, the present invention extends to a method of producing a variant human mu opioid receptor comprising an amino acid sequence having a variation in SEQ ID NO:2, wherein the variation comprises Arg260His. An example of such a method comprises the steps of culturing a unicellular host transformed or transfected with an expression vector comprising an isolated variant allele a human mu opioid receptor gene, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises G779A, operatively associated with a promoter. The transformed or transfected unicellular host is then cultured under conditions that provide for expression of the variant allele of the human mu opioid receptor gene. The variant human mu opioid receptor produced from such induced expression is then recovered from the unicellular host.

Another example comprises the steps of culturing a unicellular host transformed or transfected with an expression vector comprising an isolated nucleic acid molecule operatively associated with a promoter, wherein the isolated nucleic acid molecule is hybridizable under standard hybridization conditions to a variant allele a human mu opioid receptor gene, and the predominant or "most common" allele of a human mu opioid receptor gene found in the population comprises a DNA sequence of SEQ ID NO:1, and the variant allele comprises a DNA sequence having at least one variation in SEQ ID NO:1, wherein the at least one variation comprises G779A. The transformed or transfected unicellular host is then cultured under conditions that provide for expression of the variant allele of the human mu opioid receptor gene. The variant human mu opioid receptor produced from such induced expression is then recovered from the unicellular host.

Furthermore, the present invention extends to an isolated variant allele of a human mu opioid receptor gene, wherein the predominant or "most common" allele of the human mu opioid receptor gene comprises a DNA sequence of SEQ ID NO:1, and a variant allele of the present invention comprises a DNA sequence having at least two variations in SEQ ID NO:1, wherein the variations comprise:

A118G;

C17T;

G24A;

G779A; or

G942A.

The present invention further extends to an isolated variant allele of a human mu opioid receptor gone comprising a DNA sequence having at least two variations in SEQ ID NO:1, as stated above, which is detectably labeled. Examples of detectable labels having applications in this embodiment include, but are not limited to, a radioactive element, a chemical which fluoresces, or an enzyme.

The present invention further extends to an isolated nucleic acid molecule hybridizable under standard hybridization conditions to an isolated variant allele of a human mu opioid receptor gene, wherein the predominant or "most common" allele of the human mu opioid receptor gene comprises a DNA sequence of SEQ ID NO:1, and a variant allele of the present invention comprises a DNA sequence having at least two variations in SEQ ID NO:1, wherein the variations comprise:

A118G;

C17T;

G24A;

G779A; or

G942A.

Naturally, the present invention extends to a detectably labeled isolated nucleic acid molecule hybridizable under standard hybridization conditions to an isolated variant allele of a human mu opioid receptor comprising a DNA sequence having at least two variations in SEQ ID NO:1, wherein the variations comprise:

A118G;

C17T;

G24A;

G779A; or

G942A.

Examples of detectable labels having applications in this embodiment of the invention include, but are not limited to, a radioactive element, a chemical which fluoresces, or an enzyme.

Furthermore, the present invention extends to an isolated variant allele of a human mu opioid receptor gene comprising a DNA sequence having at least two variations in SEQ ID NO:1, as set forth above, wherein the predominant or "most common" allele of a human mu opioid receptor gene encodes a human mu opioid receptor comprising an amino acid sequence of SEQ ID NO:2, and a variant allele of the present invention encodes a human mu opioid receptor comprising an amino acid having at least two variations in SEQ ID NO:2, wherein the variations comprise:

Asn40Asp or conserved variants thereof;

Ala6Val or conserved variants thereof; or

Arg260His or conserved variants thereof.

The present invention further extends to an isolated nucleic acid molecule hybridizable under standard hybridization conditions to an isolated variant allele of a human mu opioid receptor gene comprising a DNA sequence having at least two variations in SEQ ID NO:1, wherein the variations comprise:

A118G;

C17T;

G24A;

G779A; or

G942A, such that the isolated nucleic acid molecule encodes a variant human mu opioid receptor comprising an amino acid sequence having at least two variations in SEQ ID NO:2, wherein the variations comprise:

Asn40Asp or conserved variants thereof;

Ala6Val or conserved variants thereof; or

Arg260His or conserved variants thereof.

Naturally, the present invention extends to a variant human mu opioid receptor comprising an amino acid sequence having at least two variations in SEQ ID NO:2, wherein the variations comprise:

Asn40Asp or conserved variants thereof;

Ala6Val or conserved variants thereof; or

Arg260His or conserved variants thereof.

Moreover, the present invention extends to an antibody having as an immunogen a human mu opioid receptor comprising an amino acid sequence having at least two variations in SEQ ID NO:2, wherein the variations comprise:

Asn40Asp or conserved variants thereof;

Ala6Val or conserved variants thereof; or

Arg260His or conserved variants thereof.

An antibody of the present invention can be a polyclonal antibody, a monoclonal antibody, or a chimeric antibody. Moreover, an antibody of the present invention can be detectably labeled. Examples of detectable labels having applications in an antibody of the present invention include, but are not limited to, a radioactive element, a chemical which fluoresces, or an enzyme.

Furthermore, the present invention extends to a cloning vector comprising an isolated variant allele of a human mu opioid receptor gene and an origin of replication, wherein the predominant or "most common" allele of the human mu opioid receptor gene present in the population comprises a DNA sequence of SEQ ID NO:1, and a variant allele of the present invention comprises a DNA sequence having at least two variations in SEQ ID NO:1, wherein the variations comprise:

A118G;

C17T;

G24A;

G779A; or

G942A.

In addition, the present invention extends to a cloning vector comprising an isolated nucleic acid molecule hybridizable under standard hybridization conditions to a variant allele of a human mu opioid receptor and an origin of replication, wherein the variant allele comprises a DNA sequence having at least two variations in SEQ ID NO:1, wherein the variations comprise:

A118G;

C17T;

G24A;

G779A; or

G942A, and an origin of replication.

Numerous cloning vectors have applications in this embodiment of the present invention. Examples of such vectors include, but are not limited to, *E. coli*, bacteriophages, such as lambda derivatives, plasmids such as pBR322 derivatives, and pUC plasmid derivatives such as pGEX vectors or pmal-c or pFLAG, to name only a few.

Naturally, the present invention extends to an expression vector comprising an isolated variant allele of a human mu opioid receptor gene operatively associated with a promoter, wherein such an isolated variant allele comprises a DNA sequence having at least two variations in SEQ ID NO:1, wherein the variations comprise:

A118G;

C17T;

G24A;

G779A; or

G942A.

In addition, the present invention extends to an expression vector comprising an isolated nucleic acid molecule operatively associated with a promoter, wherein the isolated nucleic acid molecule is hybridizable under standard hybridization conditions to an isolated variant allele of a human mu opioid receptor gene comprising a DNA sequence having at least two variations in SEQ ID NO:1, wherein the variations comprise:

A118G;

C17T;

G24A;

G779A; or

G942A.

Numerous promoters are available and have applications in an expression vector of the present invention. Examples of promoters having applications include, but are not limited to immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor, to name only a few.

Naturally, the present invention extends to a unicellular host transformed or transfected with an expression vector of the present invention. Examples of unicellular hosts having applications in an embodiment of the present invention include, but are not limited to, *E. coli*, Pseudonomas, Bacillus, Strepomyces, yeast, CHO, R1.1, B-W, L-M, COS1, COS7, BSC1, BSC40, BMT10 or Sf9 cells.

In another embodiment, the present invention extends to a method for producing a human mu opioid receptor comprising an amino acid sequence having at least two variations in SEQ ID NO:2, wherein the variations comprise Asn40Asp or conserved variants thereof;

Ala6Val or conserved variants thereof; or

Arg260His or conserved variants thereof.

More specifically, an example of a method for producing such a human mu opioid receptor comprises the steps of culturing a unicellular host transformed or transfected with an expression vector comprising an isolated variant allele of a human mu opioid receptor gene operatively associated with a promoter, wherein the variant allele comprises a DNA sequence having at least two variations in SEQ ID NO:1, wherein the variations comprise:

A118G;

C17T;

G24A;

G779A; or

G942A, under conditions that provide for expression of the isolated variant allele of a human mu opioid receptor gene. After expression, a variant human mu opioid receptor is recovered from the unicellular host.

In another example, a method for producing a human mu opioid receptor of the present invention comprises the steps of culturing a unicellular host transformed or transfected with an expression vector comprising an isolated nucleic acid molecule operatively associated with a promoter, wherein the isolated nucleic acid molecule is hybridizable under standard hybridization conditions to an isolated variant allele of a human mu opioid receptor gene comprising a DNA sequence having at least two variations in SEQ ID NO:1, wherein the variations comprise:

A118G;

C17T;

G24A;

G779A; or

G942A, under conditions that provide for expression of the isolated nucleic acid molecule. The variant human mu opioid receptor produced from the expression is then recovered from the unicellular host.

Moreover, Applicants have discovered that β-endorphin, an endogenous opioid comprising 31 amino acid residues, and binds to the human mu opioid receptor, has a binding affinity approximately three times greater for a variant human mu opioid receptor produced from expression of a variant allele of the human mu opioid receptor gene comprising an A118G variation in SEQ ID NO:1, than for a human mu opioid receptor produced from expression of the predominant or "most common" allele of the human mu opioid receptor gene. β-endorphin is present in both the central nervous system (CNS) and the periphery. It plays a role in endogenous analgesia, as well as in response to exposure to a potential addictive agent, such as heroin or alcohol. For example, as a neuropeptide, it can modulate neurotransmitter actions in the CNS to mediate antinociception. It is also of potential importance for the pathophysiology of addictive diseases. Given the diverse roles of β-endorphin, the presence of a variant allele of a human mu opioid receptor gene comprising at least one variation in SEQ ID NO:1, wherein the variation comprises A118G, in a subject may alter the subject's, perception of pain, susceptibility to develop opioid addiction following exposure to opioids as well as addictions to other drugs that alter the opioid system, and reaction of the subject towards a therapeutic agent designed to treat pain, such as morphine, or towards a therapeutic agent designed to treat a specific addiction.

Furthermore, Applicants have discovered a variant allele of a human mu opioid receptor gene comprising a variation in SEQ ID NO:1, wherein the variation comprises C17T, is present at a statistically significant greater frequency in the genome of at least one defined subset of addicts suffering from at least one addictive disease, than in the genomes of people not suffering from such a disease. Hence, the presence of such a variant allele of a human mu opioid receptor gene may alter perception of pain, increased or decreased susceptibility to develop opioid addiction following exposure to opioids, and influence the subject's reaction to therapeutic agents designed to treat the at least one addictive disease of the subject. Furthermore, Applicants have also discovered a variant A118G polymorphism is present in the human mu opioid receptor gene of at least one subset of nonaddicts in a statistically significant amount. Hence, the presence of the A118G polymorphism in a subject decreases the subject's perception of pain, protects the subject against potential addiction to opioids such as heroin and influences the subject's reaction to therapeutic agents designed to treat the at least one addictive disease of the subject.

Accordingly, the present invention extends to a method for determining a susceptibility in a subject to at least one addictive disease, comprising the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the variation comprises:

A118G; or

C17T.

The present of at least one of these variations in the human mu opioid receptor gene of the first allele is expected to be indicative of the subject's susceptibility to at least one addictive disease relative to the susceptibility of a standard to at least one addictive disease, wherein the standard comprises a first allele comprising a human mu opioid receptor gene having a DNA sequence of SEQ ID NO:1.

Another embodiment of the method for determining a susceptibility in the subject to at least one addictive disease, as described above, comprises the further step of determining whether the second allele of the bodily sample of the subject comprises a human mu opioid receptor gene comprising a DNA sequence having at least one variation in SEQ ID NO:1, wherein the variations comprise:

A118G; or

C17T.

The presence of at least one variation the second allele of the bodily sample is expected to be indicative of the subject's susceptibility to at least one addictive disease relative to a standard in which both alleles of a human mu opioid receptor gene comprise a DNA sequence of SEQ ID NO:1.

In particular, the presence of an A118G variation in the DNA sequence of the human mu opioid receptor gene of the first and/or second alleles in the bodily sample from the subject is expected to be indicative of a decreased susceptibility of the subject to at least one addictive disease relative to the standard.

Moreover, the presence of a C17T variation in the DNA sequence of the human mu opioid receptor gene of the first and/or second alleles in the bodily sample from the subject is expected to be indicative of an increased susceptibility of the subject to at least one addictive disease relative the susceptibility of the standard to at least one addictive disease, wherein both alleles of the standard comprise a human mu opioid receptor gene comprising a DNA sequence of SEQ ID NO:1. Examples of at least one addictive disease includes, but is not limited to opioid addiction, cocaine addiction or addiction to other psychostimulants, nicotine addiction, barbiturate or sedative hypnotic addiction, anxiolytic addiction, or alcohol addiction.

In another embodiment, the present invention extends to a method for determining a susceptibility to at least one addictive disease in a subject relative to susceptibility to at least one addictive disease in a standard, involving the detection of variations in the human mu opioid receptor itself, and particularly, determining whether a variant human mu opioid receptor is present in a bodily sample from a subject. Such a method comprises the steps of removing a bodily sample comprising a human mu opioid receptor from the subject, and determining whether the human mu opioid receptor present in the sample is a variant human mu opioid receptor of the invention, wherein the variant human mu opioid receptor comprises an amino acid sequence having at least one variation in SEQ ID NO:2, wherein the variation comprises:

Asn40Asp or conserved variants thereof; or

Ala6Val or conserved variants thereof,

The presence of at least one variation is expected to be indicative of the subject's susceptibility to at least one addictive disease relative to susceptibility to at least one addictive disease in a standard, wherein the human mu opioid receptor of the standard comprises an amino acid sequence of SEQ ID NO:2.

In particular, a variant human mu opioid receptor present in the sample comprising an amino acid sequence having at least one variation in SEQ ID NO:2, wherein the variation comprises Asn40Asp or conserved variants thereof, is expected to be indicative of a decreased susceptibility to at least one addictive disease in the subject relative susceptibility to the at least one addictive disease in the standard, wherein the human mu opioid receptor of the standard comprises an amino acid sequence of SEQ ID NO:2.

In contrast, a variant human mu opioid receptor present in a sample from the subject comprising a variation in SEQ ID NO:2, wherein the variation comprises Ala6Val or conserved variants thereof, indicates an increased susceptibility to addictive diseases in the subject relative to a standard having a human mu opioid receptor comprising an amino acid sequence of SEQ ID NO:2.

As explained above, at least one addictive disease includes, but is not limited to, opioid addiction, cocaine addiction or addiction to other psychostimulants, nicotine addiction, barbiturate or sedative hypnotic addiction, anxiolytic addiction, or alcohol addiction.

Furthermore, the present invention extends to a method for determining a susceptibility to pain in a subject relative to susceptibility to pain in a standard, comprising the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the variation comprises:

A118G; or

C17T.

The presence of at least one variation in the human mu opioid receptor gene of the first allele is expected to be indicative of a decreased or increased susceptibility to pain in the subject relative to susceptibility to pain in the standard, wherein the first allele of the standard comprises a human mu opioid receptor gene comprising a DNA sequence of SEQ ID NO:1.

Moreover, a method for determining a susceptibility to pain in a subject may further comprise the step of determining whether the second allele comprises a human mu opioid receptor gene comprising a DNA sequence having at least one variation in SEQ ID NO:1, wherein the variation comprises:

A118G; or

C17T.

The presence of the at least one variation in the human mu opioid receptor gene of the second allele of the bodily sample from the subject is expected to be indicative of an increased or decreased susceptibility to pain in the subject relative to the susceptibility to pain in the standard, wherein the second allele in the standard comprises a human mu opioid receptor gene comprising a DNA sequence of SEQ ID NO:1.

At least one variation in the human mu opioid receptor gene of the first and/or second allele of the bodily sample taken from the subject, wherein the variation comprises A118G, is expected to be indicative of a decreased susceptibility to pain in the subject relative susceptibility of pain in the standard, wherein the human mu opioid receptor gene of the first and/or second allele of the standard comprises a DNA sequence of SEQ ID NO:1.

Furthermore, the presence of at least one variation comprising C17T in the human mu opioid receptor gene of the first and/or second allele of the bodily sample from the subject is expected to be indicative of an increased susceptibility to pain in the subject relative to the susceptibility to pain in the standard, wherein the first and/or second allele of the standard comprise a human mu opioid receptor gene comprising a DNA sequence of SEQ ID NO:1.

In another embodiment, the present invention extends to a method for determining a susceptibility to pain in a subject relative to susceptibility to pain in a standard by examining a bodily sample taken from the subject for the presence of a variant human mu opioid receptor. Such a method comprises the steps of removing a bodily sample comprising a human mu opioid receptor from the subject, and determining whether the human mu opioid receptor present in the sample is a variant human mu opioid receptor of the invention, i.e., comprises an amino acid sequence having at least one variation in SEQ ID NO:2, wherein the variation comprises:

Asn40Asp or conserved variants thereof; or

Ala6Val or conserved variants thereof, such that the presence of at least one variation is expected to be indicative of the subject's susceptibility to pain relative to susceptibility to pain in the standard, wherein the human mu opioid receptor of the standard comprises an amino acid sequence of SEQ ID NO:2.

In particular, the presence of a variant human mu opioid receptor comprising an amino acid sequence having at least one variation in SEQ ID NO:2 wherein the variation comprises Asn40Asp or conserved variants thereof, is expected to be indicative of a decreased susceptibility to pain in the subject relative to susceptibility to pain in the standard, wherein the human mu opioid receptor of the standard comprises an amino acid sequence of SEQ ID NO:2.

Furthermore, the presence of a variant human mu opioid receptor comprising an amino acid sequence having a variation in SEQ ID NO:2, wherein the variation comprises Ala6Val or conserved variants thereof, in a bodily sample taken from a subject is expected to be indicative of an increased susceptibility to pain in the subject relative to susceptibility to pain in the standard, wherein the human mu opioid receptor of the standard comprises an amino acid sequence of SEQ ID NO:2.

Once a susceptibility to pain in the subject has been determined, it is possible for attending medical professionals treating the subject to administer to an appropriate, or therapeutically effective amount of pain reliever in order to induce analgesia in the subject. Administration of such an amount is important to the subject because, should an inappropriate amount of pain reliever be administered, the subject may not experience analgesia, and may be exposed to potentially deleterious side effects of the pain reliever, such as induction of addiction to the pain reliever, brain damage, or death.

Consequently, the present invention extends to a method for determining a therapeutically effective amount of pain reliever to administer to a subject in order to induce analgesia in the subject relative to a therapeutically effective amount of the pain reliever to administer to a standard in order to induce analgesia in the standard, wherein the method comprises determining a susceptibility to pain in the subject relative to susceptibility to pain in the standard. The susceptibility of pain in the subject is expected to be indicative of the therapeutically effective amount of the pain reliever to administer to the subject to induce analgesia in the subject relative to the amount of the pain reliever to administer to the standard to induce analgesia in the standard.

Hence, the present invention extends to a method for determining a therapeutically effective amount of pain reliever to administer to a subject in order to induce analgesia in the subject relative to a therapeutically effective amount of the pain reliever to administer to a standard in order to induce analgesia in the standard wherein the method comprises the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the variation comprises:

A118G; or

C17T.

The presence of at least one variation in the human mu opioid receptor gene of the first allele from the bodily sample is expected to be indicative of the therapeutically effective amount of pain reliever to administer to the subject to induce analgesia in the subject relative to the therapeutically effective amount of pain reliever to administer to the standard to induce analgesia in the standard, wherein the standard comprises a first allele comprising a human mu opioid receptor gene comprising a DNA sequence of SEQ ID NO:1.

Moreover, the present invention further extends to a method for determining a therapeutically effective amount of pain reliever to administer to a subject in order to induce analgesia in the subject relative to a therapeutically effective amount of pain reliever to administer to a standard to induce analgesia therein, further comprising the steps of removing a bodily sample comprising a first and second allele comprising a human mu opioid receptor gene from the subject, and determining whether the second allele of the bodily sample comprises a human mu opioid receptor gene comprising a DNA sequence comprising at least one variation in SEQ ID NO:1, wherein the variation comprises:

A118G; or

C17T.

The presence of at least one variation in the human mu opioid receptor gene of the first and/or second allele of the bodily sample is expected to be indicative of the therapeutically effective amount of pain reliever to administer to the subject to induce analgesia therein relative to the amount of pain reliever to administer to a standard to induce analgesia therein, wherein the first and second alleles of the standard comprise a human mu opioid receptor gene comprising a DNA sequence of SEQ ID NO:1.

More particularly, a variation of the human mu opioid receptor gene of the first and/or second allele from the bodily sample taken from the subject, comprising a DNA sequence comprising a variation in SEQ ID NO:1, wherein the variation comprises A118G, is expected to be indicative of a decreased susceptibility to pain in the subject relative susceptibility of pain in the standard. Consequently, the subject requires a decreased therapeutically effective amount of pain reliever in order to induce analgesia therein relative to the therapeutically effective amount of pain reliever needed to induce analgesia in the standard.

In contrast, a variation of the DNA sequence of the human mu opioid receptor gene of the first and/or second allele from the bodily sample taken from the subject, comprising C17T, is expected to be indicative of an increased susceptibility to pain in the subject relative to the susceptibility to pain in the standard. Hence, the therapeutically effective amount of pain reliever to administer to the subject in order to induce analgesia therein is greater than the therapeutically effective amount of pain reliever to administer to the standard to induce analgesia therein.

In another embodiment, the present invention extends to determining a therapeutically effective amount of pain reliever to administer to a subject in order to induce analgesia in the subject, by examining a bodily sample from a subject for the presence of a variant human mu opioid receptor comprising an amino acid sequence having a variation in SEQ ID NO:2. More specifically, the present invention extends to a method for determining a therapeutically effective amount of pain reliever to administer to a subject in order to induce analgesia in the subject, relative to a therapeutically effective amount of pain reliever to administer to a standard in order to induce analgesia in the standard, comprising the steps of removing a bodily sample comprising a human mu opioid receptor from the subject, and determining whether the human mu opioid receptor present in the sample comprises an amino acid sequence having at least one variation in SEQ ID NO:2, wherein the variation comprises:

Asn40Asp or conserved variants thereof; or

Ala6Val or conserved variants thereof, such that the presence of at least one variation is expected to be indicative of the therapeutically effective amount of pain reliever to administer to the subject to induce analgesia therein relative to the therapeutically effective amount of pain reliever to administer to induce analgesia in the standard, wherein the human mu opioid receptor of the standard comprises an amino acid sequence of SEQ ID NO:2.

In particular, the presence of a variant human mu opioid receptor comprising an amino acid sequence having a variation in SEQ ID NO:2, wherein the variation comprises Asn40Asp or conserved variants thereof in the sample from the subject, is expected to be indicative of a decreased therapeutically effective amount of pain reliever to administer to the subject to induce analgesia therein relative to the therapeutically effective amount of pain reliever to administer to the standard in order to induce analgesia therein.

In contrast, the presence of a variant human mu opioid receptor in the sample from the subject, wherein the receptor comprises an amino acid sequence have a variation in SEQ ID NO:2, wherein the variation comprises Ala6Val or conserved variants thereof, is expected to be indicative of an increased therapeutically effective amount of pain reliever to administer to the subject in order to induce analgesia therein relative to the therapeutically effective amount to administer to the standard to induce analgesia therein.

Examples of pain relievers having applications in this embodiment of the present invention include, but are not limited to, morphine, codeine, dihydromorphin, meperidine, methadone, fentanyl and its congeners, butorphenol, nalbuphine, LAAM, or propoxyphine, to name only a few.

Furthermore, the present invention extends to a method for determining a therapeutically effective amount of a therapeutic agent for treating at least one addictive disease to administer to a subject suffering from at least one addictive disease, relative to a therapeutically effective amount of the therapeutic agent to administer to a standard suffering from the at least one addictive disease. As a result, the dosage of therapeutic agent administered to an addict can be "tailored" to the addict's needs based upon the addict's genotype. An example of such a method comprises the steps of removing a bodily sample from the subject, wherein the bodily sample comprises a first and second allele of the human mu opioid receptor gene, and determining whether the first allele comprises a DNA sequence having at least one variation in SEQ ID NO:1, wherein the variation comprises:

A118G; or

C17T.

The presence of the at least one variation in the human mu opioid receptor gene of the first allele in the bodily sample from the subject is related to the therapeutically effective amount of therapeutic agent to administer to the subject to treat the subject's at least one addictive disease, relative to the therapeutically effective amount of the therapeutic agent to administer to the standard suffering from the at least one addictive disease, wherein the first and second allele of the standard comprise a human mu opioid receptor gene comprising a DNA sequence of SEQ ID NO:1.

Furthermore, a method for determining a therapeutically effective amount of therapeutic agent to administer to a subject suffering from at least one addictive disease may further comprise an additional step of determining whether the second allele of the bodily sample taken from the subject comprises a human mu opioid receptor gene comprises a DNA sequence having at least one variation in SEQ ID NO:1, wherein the at least one variation comprises:

A118G; or

C17T.

Such a variation in the first and/or second allele of the bodily sample is expected to be indicative of the therapeutically effective amount of the therapeutic agent to administer to the subject to treat the at least one addictive disease of the subject relative to the therapeutically effective amount of the therapeutic agent to administer to the standard suffering from the at least one addictive disease.

The presence of a human mu opioid receptor gene comprising a DNA sequence having at least one variation in SEQ ID NO:1 in the first and/or second alleles of the bodily sample taken from the subject, wherein the variation comprises A118G is expected to be indicative of a decreased therapeutically effective amount of the therapeutic agent to administer to the subject to treat the at least one addictive disease of the subject, relative to the therapeutically effective amount of the therapeutic agent to administer to the standard suffering from the at least one addictive disease, wherein the two alleles of the standard comprise a human mu opioid receptor gene comprising a DNA sequence of SEQ ID NO:1.

Furthermore, the presence of a human mu opioid receptor gene comprising a DNA sequence having at least one variation of SEQ ID NO:1 in the first and/or second allele of the bodily sample taken from the subject, wherein the variation comprises C17T, is expected to be indicative of an increased therapeutically effective amount of the therapeutic agent to administer to treat the at least one addictive disease of the subject relative to the therapeutically effective amount of the therapeutic agent to administer to the standard suffering from the at least one addictive disease to treat the at least one addictive disease in the standard, wherein the alleles of the standard comprise a human mu opioid receptor gene comprising a DNA sequence of SEQ ID NO:1.

In another embodiment, the present invention extends to determining a therapeutically effective amount of a therapeutic agent for treating at least one addictive disease to administer to a subject suffering from at least one addictive disease by examining a bodily sample from a subject for the presence of a variant human mu opioid receptor comprising an amino acid sequence having at least one variation in SEQ ID NO:2. More specifically, the present invention extends to a method for determining a therapeutically effective amount of therapeutic agent for treating at least one addictive disease to administer to a subject suffering from the at least one addictive disease, relative to a therapeutically effective amount of the therapeutic agent to administer to a standard suffering from the at least one addictive disease, wherein the method comprises the steps of removing a bodily sample comprising a human mu opioid receptor from the subject, and determining whether the human mu opioid receptor present in the sample comprises an amino acid sequence having at least one variation in SEQ ID NO:2, wherein the variation comprises:

Asn40Asp or conserved variants thereof; or

Ala6Val or conserved variants thereof.

The presence of at least one variation in the human mu opioid receptor of the bodily sample is expected to be indicative of therapeutically effective amount of the therapeutic agent to administer to the subject to treat the at least one addictive disease of the subject relative to the therapeutically effective amount of the therapeutic agent to administer to the standard suffering from the at least one addictive disease, wherein the human mu opioid receptor of the standard comprises an amino acid sequence of SEQ ID NO:2.

In particular, the presence of a variant human mu opioid receptor comprising an amino acid sequence having at least one variation in SEQ ID NO:2 comprising Asn40Asp or conserved variants thereof in the bodily sample of the subject is expected to be indicative of a decreased therapeutically effective amount of the therapeutic agent to administer to the subject to treat the at least one addictive disease in the subject relative to the therapeutically effective amount of the therapeutic agent to administer to the standard to treat the at least one addictive disease therein.

Furthermore, the presence of a variant human mu opioid receptor comprising an amino acid sequence having at least one variation in SEQ ID NO:2, wherein the variation comprises Ala6Val or conserved variants thereof in the bodily sample of the subject is expected to be indicative of an increased therapeutically effective amount of the therapeutic agent to administer to the subject in order treat the at least one addictive disease in the subject relative to the therapeutically effective amount of the therapeutic agent to administer to the standard suffering from the at least one addictive disease. Examples of at least one addictive disease includes, but is not limited to opioid addiction, cocaine addiction or addiction to other psychostimulants, nicotine addiction, barbiturate or sedative hypnotic addiction, anxiolytic addiction, or alcohol addiction. Furthermore, examples of therapeutic agents having applications of the present invention include methadone, LAAM, maltrexone, or bupinorphine, to name only a few.

Furthermore, the present invention extends to a method for diagnosing a disease or disorder related to a physiological function regulated by the HPA or HPG axes of the neuroendocrine system. The HPA and HPG axes play an important role in regulation of numerous physiological activities such as reproductive and sexual function, gastrointestinal motility, immune response to an antigen, or an ability to withstand stress. Furthermore, the HPA and HPG axes exert such regulatory control via the production of endogenous opioids that interact with opioid in many locations of the body. In particular, in the HPG axis, the mu opioid receptor is centrally involved in tonic regulation of the luteinizing hormone, particularly in its pulsatile release. Furthermore, in the HPA axis, the mu opioid receptor modulates corticotropin releasing factor/hormone (CRF or CRH) in the hypothalamus which in turn modulates production of pro-opiomelanocortin (POMC) in the pituitary which is processed into several active peptides such as ACTH, which stimulates the adrenal cortex to release the stress hormone cortisol in humans, which in turn provides the stress response to environmental stimuli. Furthermore, modulated mu opioid receptor activity can lead to modulation of most cellular and humoral immunity including that mediate through T cells, B cells, cytokines, and chemokines. The pathophysiology of immune disorders may therefore be influenced by pharmacotherapies that modulate the activity of the mu opioid receptor. Moreover, gastrointestinal motility is modulated by modulation of opioid receptor treatment, and diagnosis of a disease or disorder related to gastrointestinal motility (e.g. constipation) may be facilitated by knowledge of intrinsic mu opioid receptor motility.

Applicants have discovered that the binding affinity of an opioid receptor, such as a mu opioid receptor with an endogenous opioid ligand, such as β-endorphin, is expected to modulate such physiological activities. Hence, the binding affinity of variant mu opioid receptors explained above, for endogenous opioid ligands such as β-endorphin, is expected to modulate those physiological activities regulated by the HPA and HPG axes relative to those physiological activities in a standard having mu opioid receptors produced from the predominant or "most common" allele of the mu opioid receptor gene comprising a DNA sequence of SEQ ID NO:1. As the result, the present invention extends to a method of diagnosing a disease or disorder related to a physiological function regulated by the HPA or HPG axes. Examples of physiological functions regulated by the HPA and the HPG include, but are not limited to sexual or reproductive functions, gastrointestinal motility, immune response, or ability to withstand stress. Such a method comprises the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the variation comprises:

A118G; or

C17T.

The presence of at least one variation in the human mu opioid receptor gene of the first allele is expected to be indicative of a disorder related to a physiological function regulated by the HPA or GPA, such as sexual or reproductive functions, gastrointestinal motility, immune response, and the ability to withstand stress, wherein the first allele of the standard comprises a human mu opioid receptor gene comprising a DNA sequence of SEQ ID NO:1.

Moreover, a method for diagnosing a disease or disorder related to a physiological function regulated by the HPA or GPA, as described above may further comprise the step of determining whether the second allele of the bodily sample comprises a human mu opioid receptor gene comprising a DNA sequence having at least one variation in SEQ ID NO:1, wherein the variation comprises:

A118G; or

C17T.

The presence of the at least one variation in the human mu opioid receptor gene of the second allele of the bodily sample from the subject may be expected to be indicative of a disease or disorder related to sexual and reproductive functions, gastrointestinal motility, immune response, or the ability of the subject to withstand stress.

At least one variation in the human mu opioid receptor gene of the first and/or second allele of the bodily sample taken from the subject, wherein the variation comprises A118G, is expected to be indicative of decreased HPA and HPG activity, resulting in increased sexual or reproductive functions, increased gastrointestinal motility, increased immune response, or increased ability to withstand stress relative to the levels of such function observed in a standard.

Furthermore, the presence of at least one variation comprising C17T in the human mu opioid receptor gene of the first and/or second allele of the bodily sample from the subject is expected to be indicative increased HPA or HPG activity, resulting in decreased sexual or reproductive function, decreased gastrointestinal motility, decreased immune response, or decreased ability to withstand stress relative to the levels of such function observed in a standard.

In another embodiment, the present invention extends to a method for diagnosing a disease or disorder related to a physiological function regulated by the HPA or GPA by examining a bodily sample taken from the subject for the presence of a variant human mu opioid receptor. Such a method comprises the steps of removing a bodily sample comprising a human mu opioid receptor from the subject, and determining whether the human mu opioid receptor present in the sample is a variant human mu opioid receptor of the invention, i.e., comprises an amino acid sequence having at least one variation in SEQ ID NO:2, wherein the variation comprises:

Asn40Asp or conserved variants thereof; or

Ala6Val or conserved variants thereof, such that the presence of at least one variation is expected to be indicative of a disease or disorder related to a physiological activity regulated by the HPA or HPG axes, such as sexual function or development, gastric motility, immune response, or the ability of the subject to withstand stress, relative to regulation of such activities in a standard comprising a human mu opioid receptor having an amino acid sequence of SEQ ID NO:2.

In particular, the presence of a variant human mu opioid receptor comprising an amino acid sequence having at least one variation in SEQ ID NO:2 wherein the variation comprises Asn40Asp or conserved variants thereof, is expected to be indicative decreased HPA and HPG activity, resulting in increased sexual or reproductive functions, increased gastrointestinal motility, increased immune response, or increased ability to withstand stress relative to the levels of such function observed in a standard having a mu opioid receptor comprising an amino acid sequence of SEQ ID NO:2.

Furthermore, the presence of a variant human mu opioid receptor comprising an amino acid sequence having a variation in SEQ ID NO:2, wherein the variation comprises Ala6Val or conserved variants thereof, in a bodily sample taken from a subject is expected to be indicative of increased activity of the HPA and HPG axes, resulting in decreased sexual or reproductive functions, decreased gastrointestinal motility, decreased immune response, or decreased ability to withstand stress relative to the levels of such function observed in a standard having a mu opioid receptor comprising an amino acid sequence of SEQ ID NO:2. Examples of specific diseases or disorders related to regulation of physiological functions by the HPA or HPG axes include infertility, constipation, diarrhea, decreased immune response to antigens relative to a standard, or decreased of ability to withstand stress relative to a standard.

Once a disease or disorder related to a physiological function regulated by the HPA or HPG axes has been diagnosed, it is possible for attending medical professionals treating the subject to select and administer an appropriate therapeutic agent and a therapeutically effective amount of the agent to administer to the subject to treat such a disease or disorder. Consequently, the present invention extends to a method for determining an appropriate therapeutic agent to administer to a subject suffering from a disease or disorder related to a physiological function regulated by the HPA or HPG axes, comprising removing a bodily sample from the subject, and determining the presence of at least one variant allele of a mu opioid receptor gene in the bodily sample, wherein the variant allele comprises a human mu pioid receptor gene comprising a DNA sequence having at least one variation in SEQ ID NO:1, wherein the variation comprises:

A118G; or

C17T.

The present invention further extends to a method for selecting an appropriate therapeutic agent to administer to a subject suffering from a disease or disorder related to a physiological function regulated by the HPA or HPG axes as set forth above, further comprising determining whether the bodily sample comprises a second variant allele of the mu opioid receptor gene comprising a DNA sequence having a variation in SEQ ID NO:1, wherein the variation comprises:

A118G; or

C17T.

In particular, should either or both alleles of the mu opioid receptor gene of the bodily sample comprise a DNA sequence having a variation in SEQ ID NO:1, wherein the variation comprises A118G, the mu opioid receptors of the subject are expected to have increased function relative to mu opioid receptors of a standard produced from expression of the predominant or "most common" mu opioid receptor allele comprising a DNA sequence of SEQ ID NO:1. This increased function is expected to result in decreased function of the HPA and HPG axes. Hence, an appropriate therapeutic agent for treating a disease or disorder related to decreased activity of the HPA or HPG axes, such as diarrhea can be selected.

In contrast, a human mu opioid receptor produced from expression of a variant allele of a mu opioid receptor gene comprising a variation in SEQ ID NO:1, wherein the variation comprises C17T is expected to have decreased activity relative to a mu opioid receptor produced from expression of the predominant or "most common" allele of the human mu opioid receptor gene comprising a DNA sequence of SEQ ID NO:1. This decreased activity is expected to result in higher activity of the HPA and HPG axes. As a result, a medical professional attending the subject is able to select an appropriate therapeutic agent for treating a disease or disorder related to sexual and reproductive functions, such as infertility, gastrointestinal motility, such as constipation or diarrhea, decreased immune response towards antigens relative to immune response in a standard, or decreased ability to withstand stress relative to ability to withstand stress in a standard.

The present invention further extends to commercial test kits suitable for use by a medical professional to determine whether either or both alleles of a bodily sample taken from a subject comprise a DNA sequence having at least one variation in SEQ ID NO:1, wherein the variation comprises:

A118G; or

C17T.

Commercial test kits of the present invention have applications in determining susceptibility of pain in the subject relative to a standard. Such kits can also be used to determine a subject's increased or decreased susceptibility to at least one addictive disease relative to susceptibility to at least one addictive disease in a standard. Also a therapeutically effective amount of pain reliever to administer to the subject in order to induce analgesia in the subject relative to a therapeutically effective amount of pain reliever to administer to a standard to induce analgesia in the standard can be determined. Moreover, a test kit of the present invention has applications in determining a therapeutically effective amount of therapeutic agent for treating at least one addictive disease to administer to a subject suffering from the at least one addictive disease, relative to a therapeutically effective amount of therapeutic agent to administer to a standard suffering from at least one addictive disease. Furthermore, test kits of the invention have applications in diagnosing a disease or disorder related to a physiological condition regulated by the HPA or HPG axes of the neuroendocrine system, and in selecting an appropriate therapeutic agent for treating such a disease or disorder, along with a therapeutically effective amount of agent to administer to the subject. A standard as used herein comprises two alleles of a human mu opioid receptor gene comprising a DNA sequence of SEQ ID NO:1.

Furthermore, a commercial test kit of the present invention can also be used to determine the presence of an isolated variant allele of a human mu opioid receptor gene of the present invention in a bodily sample removed from a subject, which can serve as a genetic marker. As explained above, the predominant or "most common" allele of a human mu opioid receptor gene found in the population comprises a DNA sequence of SEQ ID NO:1. Hence a variant allele comprising a DNA sequence having a variation in SEQ ID NO:1, wherein the variation comprises:

G24A;

G779A; or

G942A, or combinations thereof, can be detected in the bodily sample with a commercial kit of the invention.

Other variant alleles of the human mu opioid receptor gene of the present invention can be detected with a commercial test kit of the present invention. For example, an isolated variant allele of a human mu opioid receptor gene detectable with a commercial kit of the present invention, comprises a DNA sequence having at least two variations in SEQ ID NO:1, wherein the variations comprise:

A118G;

C17T;

G24A;

G779A; or

G942A.

Accordingly, a commercial test kit may be prepared for determining the presence of at least one variation in a human mu opioid receptor gene of either or both alleles in a bodily sample taken from a subject, wherein the commercial test kit comprises:

a) PCR oligonucleotide primers suitable for detection of an allele comprising a human mu opioid receptor gene having a DNA sequence with a variation in SEQ ID NO:1;

b) other reagents; and c) directions for use of the kit.

The present invention further extends to commercial test kits capable of detecting a variant human mu opioid receptor in a bodily sample taken from a subject. Examples of variant human mu opioid receptors that can be detected with a kit of the present invention comprise:

a variant human mu opioid receptor comprising an amino acid sequence having a variation in SEQ ID NO:2, wherein the variation comprises Arg260His or conserved variants thereof; or a variant human mu opioid receptor comprising an amino acid sequence having at least two variations in SEQ ID NO:2, wherein the variations comprise:

Asn40Asp or conserved variants thereof;

Ala6Val or conserved variants thereof; or

Arg260His or conserved variants thereof.

Moreover, a commercial test kit of the present invention can be used to determine: susceptibility to pain in the subject relative to susceptibility to pain in a standard; a therapeutically effective amount of pain reliever to administer to a subject to induce analgesia in the subject relative to a therapeutically effective amount of pain reliever to administer to a standard to induce analgesia in the standard; a therapeutically effective amount of therapeutic agent for treating at least one addictive disease to administer to a subject suffering from at least one addictive disease, relative to a therapeutically effective amount of therapeutic agent to administer to a standard suffering from the at least one addictive disease; diagnosing a disease or disorder related to a physiological condition regulated by the HPA or HPG axes of the neuroendocrine system, or selecting an appropriate therapeutic agent for treating such a disease or disorder, along with a therapeutically effective amount of such agent to administer to the subject. Accordingly, the present invention extends to a commercial test kit having applications set forth above, comprising a predetermined amount of at least one detectably labeled immunochemically reactive component having affinity for a variant human mu opioid receptor;

(b) other reagents; and (c) directions for use of the kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the human mu opioid receptor of a bodily sample to a detectable label;

(b) one or more additional immunochemical reagents of which at least one reagent is a ligand or an immobilized ligand, which ligand comprises:

(i) a ligand capable of binding with the labeled component (a);

(ii) a ligand capable of binding with a binding partner of the labeled component (a);

(iii) a ligand capable of binding with at least one of the component(s) to be determined; or (iv) a ligand capable of binding with at least one of the binding partners of at least one of the component(s) to be determined; or (c) directions for the performance of a protocol for the detection and/or determination of one or more components of an immunochemical reaction between the human mu opioid receptor gene of the present invention and a specific binding partner thereto.

Accordingly, it is an object of the present invention to provide heretofore unknown variations the DNA sequence of the human mu opioid receptor gene wherein the variations can be used to map the locus of the human mu opioid receptor gene.

It is yet another object of the present invention to use heretofore unknown polymorphisms of an allele of the human mu opioid receptor gene as markers for any kind of disorder related to the human mu opioid receptor, such as an addictive disease, pain, or markers for genes.

It is another object of the present invention to provide nucleotides, optionally detectably labeled, hybridizable under standard hybridization conditions to variant alleles of the human mu opioid receptor gene disclosed herein, as well as polypeptides produced from the expression of the variant alleles and nucleotides hybridizable thereto under standard hybridization conditions.

It is yet another object of the present invention to provide antibodies, optionally detectably labeled, having immunogens comprising polypeptides produced from the expression of variant alleles of human mu opioid receptor gene, or expression of isolated nucleic acid molecules hybridizable under standard hybridization conditions to variant alleles disclosed herein.

It is another object of the present invention to gain insight into a subject's susceptibility to pain. This insight can be used to determine a therapeutically effective dose of pain reliever to administer to the subject to induce analgesia therein relative to the therapeutically effective amount of pain reliever administered to a standard to induce analgesia therein, wherein the standard comprises two alleles of the human mu opioid receptor gene comprising a DNA sequence of SEQ ID NO:1, or a variant human mu opioid receptor comprising an amino acid sequence of SEQ ID NO:2.

Such information can be used to tailor a regimen for treating a subject suffering from at least one addictive disease, relative to the therapeutically effective amount of therapeutic agent administered to a standard suffering from at least one addictive disease.

It is yet another object of the present invention to provide commercial test kits for attending medical professionals to determine the presence of variant alleles of a human mu opioid receptor gene in a bodily sample taken from a subject. The results of such testing can then be used to determine the subject's susceptibility to pain, susceptibility to at least one addictive disease, determining a therapeutically effective amount of pain reliever to administer to the subject in order to induce analgesia, or determining a therapeutically effective amount of therapeutic agent for treating at least one addictive disease to administer to the subject.

It is an object of the present invention to determine the activity of a mu opioid receptor in a subject, and use such information to diagnose a disease or disorder related to sexual or reproductive function, gastrointestinal motility, immune response, or ability to withstand stress, wherein variant alleles of the mu opioid receptor gene when expressed produce variant mu opioid receptors having activity different from a mu opioid receptor produced from the predominant or "most common" allele of the mu opioid receptor comprising a DNA sequence of SEQ ID NO:1.

It is another object of the present invention to employ Applicants' discovery of a correlation between the activity of a mu opioid and its impact the neuroendocrine system, and particularly on levels of hormones within the body. As a result, the level of activity of the mu opioid receptor effects sexual or reproductive function, gastrointestinal motility, immune response, or ability to withstand stress. Such information can further be used select appropriate therapeutic agents to treat diseases such as infertility, constipation, or diarrhea.

Further, such information can be used to select appropriate therapeutic agents to increase immune response against an antigen such as a bacterium, a virus or a tumor cell in the subject, and to treat psychiatric diseases or disorders such as obsessive compulsive disorder, schizophrenia, or depression.

It is yet another object of the present invention to provide commercial detecting variant alleles of the human mu opioid receptor gene or the presence of a variant human mu opioid receptor in a bodily sample taken from a subject. The results of such tests can then be used to gain incite into a subject's ability to withstand pain, susceptibility to addiction, to diagnose a disease or disorder related to a physiological function regulated by the HPA or HPG axes such as sexual and reproductive functions, gastrointestinal motility, immune response, and the ability of the subject to withstand stress.

These and other aspects of the present invention will be better appreciated by reference to the following drawings and Detailed Description.

BRIEF DESCRIPTION OF THE DRAWINGS

FIG. 4: The nucleic acid sequence of the most common allele of the mu opioid receptor (SEQ ID NO:1) (GENBANK accession number L25119).

FIG. 5: Amino acid sequence of the most common human mu opioid receptor (SEQ ID NO:2) referred to hMOR1, which is compared to the rat homologs of the mu (rMOR1) (SEQ ID NO:3), delta (rDOR1) (SEQ ID NO:4) and kappa (rKOR) (SEQ ID NO:5) opioid receptor amino acid sequences by the use the program PILEUP. Boldface type and shading, transmembrane domain candidates; *, consensus sites for N-linked glycosylation; italics, amino acid residues different between rat and human mu opioid receptor; @, indicates intron/exon boundary.

DETAILED DESCRIPTION OF THE INVENTION

Figure 1:
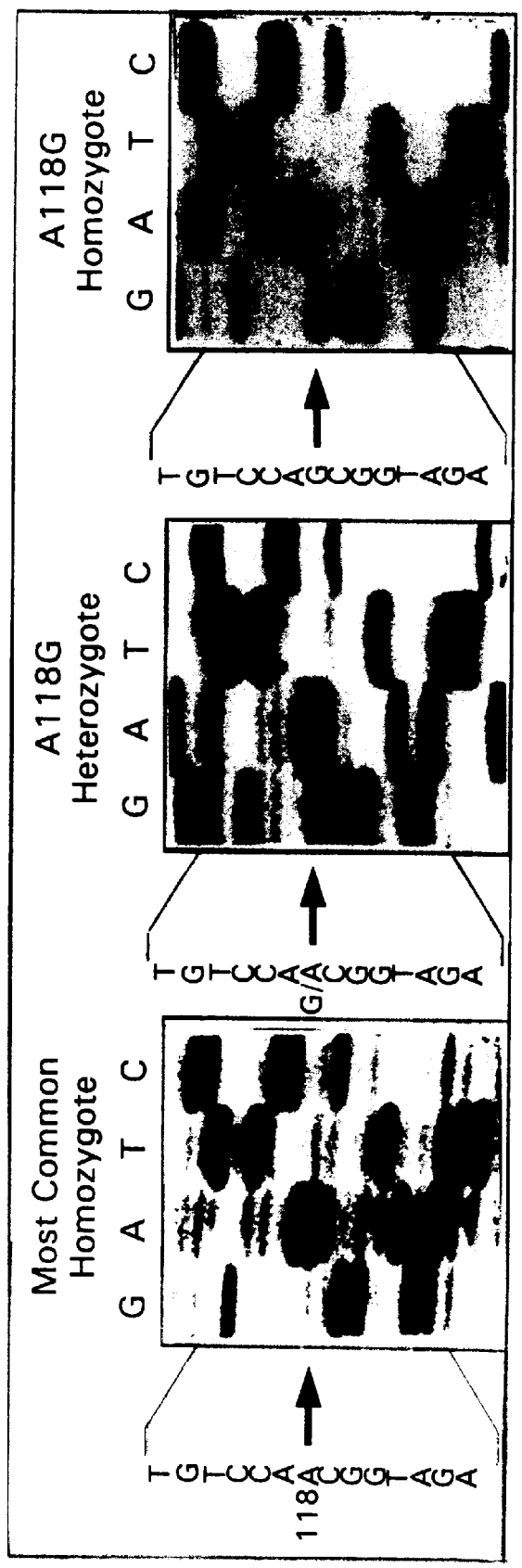
FIG. 1: DNA sequence of the A118G polymorphism. Examples of DNA sequences are shown from individuals homozygous for the most common allele (left) (SEQ ID NO:1), heterozygous (center) and homozygous for the A118G variant allele (right). The arrows indicate the position of nucleotide 118, with the adjacent sequences shown.
Figure 2A:
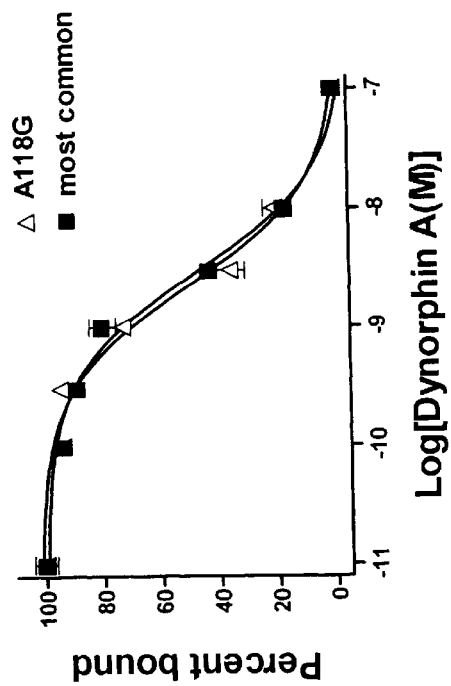
FIG. 2: Binding of endogenous opioid peptides to the most common (SEQ ID NO:2) and Asn40Asp mu opioid receptors. Membrane preparations from cells expressing either the most common (open circles) or the A118G variant (filled squares) receptors were used in binding experiments to displace the [3H]-DAMGO binding. Shown are examples of displacement binding for four endogenous peptides: Met-enkephalin, dynorphin A, β-endorphin, and endomorphin-1.
Figure 2B:
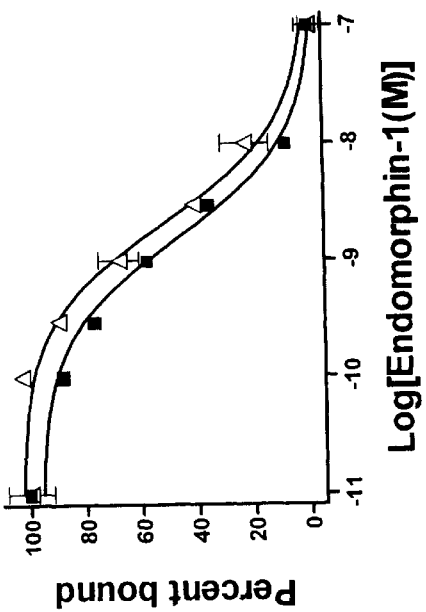
Figure 2C:
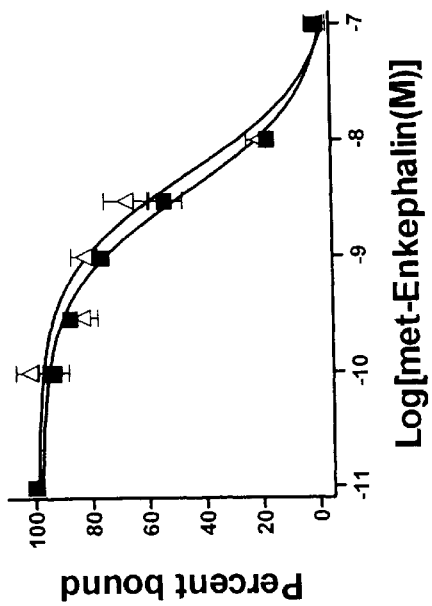
Figure 2D:
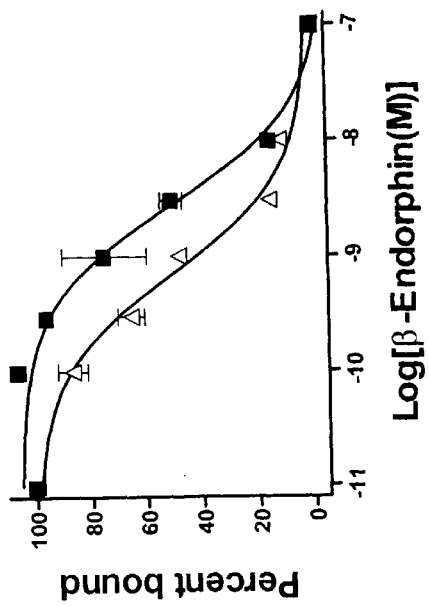

As explained above, the present invention is based upon Applicants' surprising and unexpected discovery of heretofore unknown single nucleotide polymorphisms (SNPs) in the human mu opioid receptor, along with combinations thereof. Furthermore, Applicants have discovered that more than one SNP can be present in either or both alleles of the human mu opioid receptor gene in a subject.

In addition, the present invention is based upon Applicants' surprising discovery of molecules of heretofore unknown isolated nucleic acid molecules which encode human mu opioid receptors, wherein the DNA sequences include a combination of presently known polymorphisms and subsequently of the human mu opioid receptors discovered by Applicants and set forth herein.

Furthermore, the present invention is based upon Applicants' surprising and unexpected discovery that the expression of variant alleles of the human mu opioid gene comprising a DNA sequence having a variation in SEQ ID NO:1, wherein the variations comprise A118G or C17T, produce a variant mu opioid receptor comprising an amino acid sequence having a variation in SEQ ID NO:2, wherein the variations comprise Asn40Asp or Ala6Val, and that these variant receptors exhibit a binding affinity for β-endorphin that is different from the binding affinity of a mu opioid receptor comprising an amino acid sequence of SEQ ID NO:2, and is encoded by the predominant or "most common" allele of the mu opioid receptor gene comprising a DNA sequence of SEQ ID NO:1.

Furthermore, the present invention is based upon Applicants' prediction that variant alleles of the mu opioid receptor gene, which comprise a DNA sequence having a variation in SEQ ID NO:1, wherein the variation comprises A118G or C17T encode variant mu opioid receptors comprising amino acid sequence having a variation in SEQ ID NO:2 wherein the variation comprises Asn40Asp or Ala6Val, and the variant receptors have an activity in vivo different from the of the predominant or "most common" mu opioid receptor, the presence of such variant alleles in a bodily sample from a subject is expected to be indicative of the activity of the mu opioid receptors in the subject.

The present invention further extends to heretofore unknown polymorphisms of the human mu opioid receptor gene that can serve as genetic markers to map the locus of the human mu opioid receptor gene.

Moreover, the present invention extends to the characterization of the binding properties of human mu opioid receptors produced from the expression of nucleic acid molecules comprising DNA sequences with such heretofore unknown polymorphisms of the human mu opioid receptor gene, or combinations of heretofore unknown polymorphisms and known polymorphisms. In particular, the human mu opioid receptor is the major pharmacological target for clinically important opioid alkaloids, including morphine, methadone and fentanyl, as well as for endogenous opioid peptides such as β-endorphin, Met-enkephalin-Arg-Phe, the recently identified endomorphins [Zadina, J. E., Hackler, L., Ge, L. J. & Kastin, A. J. (1997) *Nature* 386, 499–502, which is hereby incorporated by reference in its entirety] and other opioid drugs [Pasternak, G. W. (1993) *Clin. Neuropharmacol.* 16, 1–18, which is hereby incorporated by reference herein in its entirety]. Applicants have discovered that, surprisingly, human β-endorphin, an endogenous opioid, has a much higher binding affinity for a human mu opioid receptor produced from expression of the A118G variant allele of the human mu opioid receptor gene than for a human mu opioid receptor protein produced from the expression of the predominant or "most common" allele of the human mu opioid receptor gene (SEQ ID NO:1) comprising a DNA sequence of SEQ ID NO:1, and that a variant receptor encoded by a variant allele comprising a DNA sequence of SEQ ID NO:1, wherein the variation comprises A118G has increased activity relative to the predominant or "most common" allele. This increased activity is expected to result in lower activity of the HPA and HPG axes. As a result sexual and reproductive functions, gastrointestinal motility, immune response and/or ability to withstand stress are increased in the subject relative to the levels of such functions in a standard comprising two alleles of the mu opioid receptor gene comprising a DNA sequence of SEQ ID NO:1.

In contrast, a human mu opioid receptor produced from expression of the C17T variant allele of the human mu opioid receptor gene has decreased binding affinity for β-endorphin relative to the binding affinity of a human mu opioid receptor protein produced from the expression of the predominant or "most common" allele of the human mu opioid receptor gene (SEQ ID NO:1) comprising a DNA sequence of SEQ ID NO:1. Consequently, a variant receptor encoded by a C17T variant allele exhibits decreased activity relative to the predominant or "most common" allele. This decreased activity results in increased activity of HPA and HPG axes. Hence, sexual and reproductive functions, gastrointestinal motility, immune response and/or ability to withstand stress are decreased in the subject relative to the levels of such physiological functions in a standard comprising two alleles of the mu opioid receptor gene comprising a DNA sequence of SEQ ID NO:1.

Furthermore, the present invention extends to characterizing the activity of such heretofore unknown human mu opioid receptors produced from the expression of isolated nucleic acid molecules of the present invention. More particularly, the increased or decreased ability of such human mu opioid receptors produced from isolated nucleic acid acids of the present invention to activate G protein-activated inwardly rectifying K+ (GIRK) channels via a G protein-mediated mechanism can be determined, and is expected to be indicative of activity.

The present invention further extends to Applicants' discovery that polymorphisms such as A118G and C17T, are present in the population at a high frequency (greater than 5%), and that the presence of such polymorphisms in the human mu opioid receptor gene of a subject correlates to an increased or decreased susceptibility to addictive diseases, such as heroin addiction, cocaine addiction, or alcohol addiction, to name only a few, and modulation of physiological functions regulated by the HPA and HPG axes, such as sexual and reproductive functions, gastrointestinal motility, immune response and/or ability to withstand stress, relative to such functions in a standard.

The present invention extends to diagnostic methods to determine a subject's increased or decreased susceptibility to at least one addictive disease. With the results of such methods, targeted prevention methods, early therapeutic intervention, and improved chronic treatment to opioid addiction are set forth herein and encompassed by the present invention. In addition, attending medical professionals of subjects armed with the results of such diagnostic methods can determine whether administration of opioid analgesics is appropriate or whether non-opioid derived analgesics should be administered to the subject. Also, appropriate choice and type of analgesic can be made in treating a subject's pain.

Also, the present invention extends to methods of determining a subject's increased or decreased susceptibility to pain and response to analgesics, and using that information when prescribing analgesics to the subject.

Furthermore, the present invention extends to diagnosing a disease or disorder related to a physiological function regulated by the HPA and HPG axes, such as sexual and reproductive functions, gastrointestinal motility, immune response, and the ability to withstand stress.

The present invention further extends to variant alleles of the human mu opioid receptor gene comprising a DNA sequence comprising a heretofore unknown polymorphism, such as:

G24A;

G779A; or

G942A, or combinations thereof.

Furthermore, Applicants' invention extends to variant alleles of the human mu opioid receptor gene comprising a DNA sequence having at least two variations in the predominant or "most common" allele comprising a human mu opioid receptor gene comprising a DNA sequence of SEQ ID NO:1, wherein the variations comprise

A118G;

C17T;

G24A;

G779A; or

G942A, or a combination thereof.

Furthermore, the present invention is based on Applicants' discovery that surprisingly and unexpectedly, the C17T variant allele of the human mu opioid receptor is present in a statistically significantly higher frequency in opioid dependent persons than in persons not addicted to opioids.

Consequently, an initial aspect of the present invention involves isolation of heretofore unknown variant alleles of the human mu opioid receptor gene. As used herein, the term "gene" refers to an assembly of nucleotides that encode a polypeptide, and includes cDNA and genomic DNA nucleic acids.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the MRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 20 nucleotides; and more preferably the length is at least about 30 nucleotides; and most preferably 40 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" or "promoter" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A coding sequence is "operatively associated with" a transcriptional and translational control sequences, such as a promoter for example, when RNA polymerase transcribes the coding sequence into mRNA, which in turn is translated into a protein encoding by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

As explained above, within the scope of the present invention are DNA sequences encoding variant alleles of a human mu opioid receptor gene of the present invention, which comprise at least one variation in the predominant or "most common" allele of the human mu opioid receptor gene. The most common allele comprises a DNA sequence of SEQ ID NO:1, and variations in the most common allele comprise:

G24A;

G779A; or

G942A, or combinations thereof.

In another embodiment, the present invention comprises DNA sequences encoding variant alleles of a human mu opioid receptor gene, comprising at least two variations in the predominant or "most common" allele of the human mu opioid receptor gene, wherein the most common human mu opioid receptor gene comprises a DNA sequence of SEQ ID NO:1. Variant alleles of the human mu opioid receptor gene encompassed by the present invention comprise a DNA sequence comprising at least two variations of SEQ ID NO:1, wherein the variation comprises:

G24A;

G779A;

G942A;

A118G; or

C17T.

Moreover, due to degenerate nature of codons in the genetic code, variant human mu opioid receptor proteins encoded by variant alleles of the present invention, wherein the variant human mu opioid receptors comprise an amino acid sequence having at least one variation in SEQ ID NO:2, wherein the variations comprise:

Asn40Asp or conserved variants thereof;

Ala6Val or conserved variants thereof; or

Arg260His or conserved variants thereof, or combinations thereof, can be encoded by nucleic acid molecules other than those set forth above. "Degenerate nature" refers to the use of different three-letter codons to specify a particular amino acid pursuant to the genetic code. It is well known in the art that the following codons can be used interchangeably to code for each specific amino acid:

```
Phenylalanine (Phe or F)  UUU or UUC

Leucine (Leu or L)        UUA or UUG or CUU or CUC or CUA or CUG

Isoleucine (Ile or I)     AUU or AUC or AUA

Methionine (Met or M)     AUG

Valine (Val or V)         GUU or GUC of GUA or GUG

Serine (Ser or S)         UCU or UCC or UCA or UCG or AGU or AGC

Proline (Pro or P)        CCU or CCC or CCA or CCG

Threonine (Thr or T)      ACU or ACC or ACA or ACG

Alanine (Ala or A)        GCU or GCG or GCA or GCG

Tyrosine (Tyr or Y)       UAU or UAC

Histidine (His or H)      CAU or CAC

Glutamine (Gin or Q)      CAA or CAG

Asparagine (Asn or N)     AAU or AAC
```

-continued

| | |
|---|---|
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

A variant allele of the human mu opioid receptor gene of the present invention, whether genomic DNA or cDNA, can be isolated from any source, particularly from a human cDNA or genomic library. Methods for obtaining an allele of a human mu opioid receptor gene, variants thereof, or the most common, are well known in the art, as described above (see, e.g., Sambrook et al., 1989, supra).

Accordingly, any human cell potentially can serve as the nucleic acid source for the molecular cloning of a variant allele of the human mu opioid receptor gene of the present invention, or a nucleic acid molecule hybridizable to a variant allele of a human mu opioid receptor gene of the present invention. The DNA may be obtained by standard procedures known in the art from cloned DNA (e.g., a DNA "library"), and preferably is obtained from a cDNA library prepared from tissues with high level expression of a human mu opioid receptor protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U. K. Vol. I, II). Clones derived from genomic DNA may contain regulatory and intron DNA regions in addition to coding regions; clones derived from cDNA will not contain intron sequences. Whatever the source, an allele of a human mu opioid receptor gene of the present invention should be molecularly cloned into a suitable vector for propagation.

In the molecular cloning of a human mu opioid receptor gene of the present invention, DNA fragments are generated, some of which will encode an allele. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing an allele of a human mu opioid receptor of the present invention may be accomplished in a number of ways. For example, if an amount of a portion of an allele of a human mu opioid receptor gene, or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained for a human mu opioid receptor protein can be prepared and used as probes for DNA encoding a variant allele of a human mu opioid receptor gene of the present invention, as was done in a specific example, infra, or as primers for cDNA or mRNA (e.g., in combination with a poly-T primer for RT-PCR). Preferably, a fragment is selected that is highly unique to a variant allele of the human mu opioid receptor gene of the invention. Those DNA fragments with substantial homology to the probe will hybridize. As noted above, the greater the degree of homology, the more stringent hybridization conditions can be used.

Further selection can be carried out on the basis of the properties of an allele of a human mu opioid receptor gene of the present invention e.g., if the allele encodes a variant human mu opioid receptor protein having an isoelectric, electrophoretic, amino acid composition, or partial amino acid sequence different from that produced from the expression of the most common allele of a human mu opioid receptor gene (SEQ ID NO:1) herein. Thus, the presence of an allele of a human mu opioid receptor gene of the present invention may be detected by assays based on the physical, chemical, or immunological properties of its expressed product. For example, cDNA clones, or DNA clones which hybrid-select the proper mRNAs, can be selected which produce a protein that, e.g., has different electrophoretic migration, isoelectric focusing or non-equilibrium pH gel electrophoresis behavior, proteolytic digestion maps, or antigenic properties as known for a human mu opioid receptor produced from expression of a most common allele of the human mu opioid receptor gene (SEQ ID NO:1).

An allele of a human mu opioid receptor gene of the present invention can also be identified by MRNA selection, i.e., by nucleic acid hybridization followed by in vitro translation. In this procedure, nucleotide fragments are used to isolate complementary mRNAs by hybridization. Such DNA fragments may represent available, purified DNA of an allele of a human mu opioid receptor gene of the present invention, or may be synthetic oligonucleotides designed from the partial amino acid sequence information. Immunoprecipitation analysis or functional assays of the in vitro translation products of the products of the isolated mRNAs identifies the mRNA and, therefore, the complementary DNA fragments, that contain the desired sequences.

A labeled cDNA of an allele of a human mu opioid receptor gene of the present invention, or fragments thereof, or a nucleic acid hybridizable under standard hybridization conditions to an allele of a human mu opioid receptor gene of the present invention, can be synthesized using sequences set forth herein. The radiolabeled MRNA or cDNA may then be used as a probe to identify homologous DNA fragments from among other genomic DNA fragments. Suitable labels include enzymes, radioactive isotopes, fluorophores (e.g., fluorescene isothiocyanate (FITC), phycoerythrin (PE), Texas red (TR), rhodamine, free or chelated lanthanide series salts, especially $Eu^{3}+$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^{3}H$, $^{14}C$, $^{32}p$, $35S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-a 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Other labels for use in the invention include magnetic beads or magnetic resonance imaging labels.

Cloning Vectors

The present invention also relates to cloning vectors comprising variant alleles of a human mu opioid receptor gene of the present invention, and an origin of replication. For purposes of this Application, an "origin of replication refers to those DNA sequences that participate in DNA synthesis.

As explained above, in an embodiment of the present invention, variant alleles of a human mu opioid receptor gene of the present invention comprise a DNA sequence having at least one variation in the most common allele of a human mu opioid receptor gene comprising a DNA sequence of SEQ ID NO:1, wherein the variation comprises:

G24A;

G779A; or

G942A, or combinations thereof.

In another embodiment, the present invention extends to variant alleles of a human mu opioid receptor gene, comprising a DNA sequence having at least two variations in the DNA sequence of SEQ ID NO:1, wherein the variations comprise:

G24A;

G779A;

G942A;

A118G; or

C17T.

Furthermore, an isolated variant allele of a human mu opioid receptor gene of the present invention, or isolated nucleic acid molecules hybridizable under standard hybridization conditions to an isolated variant allele of a human mu opioid receptor gene of the present invention, can be inserted into an appropriate cloning vector in order to produce multiple copies of the variant allele or isolated nucleic acid molecule. A large number of vector-host systems known in the art may be used. Possible vectors include, but are not limited to, plasmids or modified viruses. The vector system used however must be compatible with the host cell used. Examples of vectors include having applications herein, but are not limited to *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating a variant allele of the human mu opioid receptor gene of the present invention, or an isolated nucleic acid hybridizable thereto under standard hybridization conditions, into a cloning vector which has complementary cohesive termini. However, if the complementary restriction sites used to fragment the variant allele or isolated nucleic acid hybridizable thereto are not present in the cloning vector, the ends of the variant allele or the isolated nucleic acid molecule hybridizable thereto under standard hybridization conditions may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Such recombinant molecules can then be introduced into host cells via transformation, transfection, infection, electroporation, etc., so that many copies of a variant allele of a human mu opioid receptor gene of the present invention, or an isolated nucleic acid molecule hybridizable thereto under standard hybridization conditions, can be generated. Preferably, the cloned isolated variant is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E. coli plasmid with sequences from the yeast 2 $\mu$plasmid.

In an alternative method an isolated variant allele of a human mu opioid receptor gene of the present invention or an isolated nucleic acid molecule hybridizable thereto under standard hybridization conditions may be identified and isolated after insertion into a suitable cloning vector in a "shot gun" approach. Enrichment for a variant allele, for example, by size fractionation, can be done before insertion into the cloning vector.

Expression Vectors

As stated above, the present invention extends to an isolated variant allele of a human mu opioid receptor gene, comprising a DNA sequence having at least one variation in the DNA sequence of the predominant or "most common" allele of the human mu opioid receptor gene comprising a DNA sequence of SEQ ID NO:1 wherein the variations comprise:

G24A;

G779A; or

G942A, or combinations thereof.

In another embodiment, the present invention extends to an isolated variant allele of a human mu opioid receptor gene, a DNA sequence having at least two variations in the predominant or "most common" allele of the human mu opioid receptor gene comprising a DNA sequence of SEQ ID NO:1 wherein the variations comprise:

G24A;

G779A;

G942A;

A118G; or

C17T.

Variant alleles of the present invention, along with isolated nucleic acid molecules hybridizable to such variant alleles under standard hybridization conditions, can be inserted into an appropriate expression vector, i.e., a vector which contains the necessary elements for the transcription and translation of the inserted protein-coding sequence. Thus, a variant allele of the present invention, or an isolated nucleic acid molecule hybridizable to a variant allele of the present invention under standard hybridization conditions, is operatively associated with a promoter in an expression vector of the invention. A DNA sequence is "operatively associated" to an expression control sequence, such as a promoter, when the expression control sequence controls and regulates the transcription and translation of that DNA sequence. The term "operatively associated" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a variant allele of the present invention, or an isolated nucleic acid hybridizable thereto under standard hybridization conditions does not contain an appropriate start signal, such a start signal can be inserted into the expression vector in front of (5' of) the molecule.

Both cDNA and genomic sequences can be cloned and expressed under control of such regulatory sequences. An expression vector also preferably includes a replication origin.

The necessary transcriptional and translational signals can be provided on a recombinant expression vector, or they may be supplied by an allele comprising a human mu opioid receptor gene.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A variant allele of a human mu opioid receptor gene of the present invention or an isolated nucleic acid molecule hybridizable thereto under standard hybridization conditions may be expressed chromosomally, after integration of the coding sequence by recombination. In this regard, any of a number of amplification systems may be used to achieve high levels of stable gene expression (See Sambrook et al., 1989, supra).

A unicellular host transformed or transfected with an expression vector of the present invention is cultured in an appropriate cell culture medium that provides for expression by the unicellular host of the variant allele, or isolated nucleic acid hybridizable thereto under standard hybridization conditions.

Any of the methods previously described for the insertion of DNA fragments into a cloning vector may be used to construct expression vectors of the present invention. These methods may include in vitro recombinant DNA and synthetic techniques and in vivo recombination (genetic recombination).

Expression of a variant allele of a human mu opioid receptor gene of the present invention or an isolated nucleic acid molecule hybridizable to a variant allele of a human mu opioid receptor gene under standard hybridization conditions, may be controlled by any promoter/enhancer element known in the art, but these regulatory elements must be functional in the host selected for expression. Promoters which may be used to control expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadal releasing hormone gene control region which is active in the hypothalamus (Mason et al., 1986, Science 234:1372–1378).

Moreover, expression vectors comprising a variant allele of a human mu opioid receptor gene of the present invention, or an isolated nucleic acid molecule hybridizable thereto under standard hybridization conditions, can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the variant allele or isolated nucleic acid molecule hybridizable thereto under standard hybridization conditions can be amplified by PCR to provide for detection of the amplified product. In the second approach, the presence of a foreign gene inserted into an expression vector of the present invention can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In yet another example, if an isolated variant allele of a human mu opioid receptor gene of the present invention, or an isolated nucleic acid molecule hybridizable thereto under standard hybridization conditions, is inserted within the "selection marker" gene sequence of the vector, recombinants containing the insert can be identified by the absence of the inserted gene function. In the fourth approach, recombinant expression vectors can be identified by assaying for the activity, biochemical, or immunological characteristics of the gene product expressed by the recombinant, provided that the expressed protein assumes a functionally active conformation.

Naturally, the present invention extends to a method of producing a variant human mu opioid receptor comprising an amino acid sequence having at least one variation in the amino acid sequence of SEQ ID NO:2, wherein the variation comprises Arg260His or conserved variants thereof. An example of such a method comprises the steps of culturing a unicellular host transformed or transfected with an expression vector comprising a variant allele of a human mu opioid receptor gene comprising a DNA sequence having a variation in SEQ ID NO:1, wherein the variation comprises G779A, wherein the variant allele which is operatively associated with a promoter. The transformed or transfected unicellular host is then cultured under conditions that provide for expression of the variant allele of the human mu opioid receptor gene, and the expression product is recovered from the unicellular host.

Another example involves culturing a unicellular host transformed or transfected with an isolated nucleic acid molecule hybridizable under standard hybridization conditions to a variant allele of a human mu opioid receptor gene comprising a DNA sequence having at least one variation in SEQ ID NO:1, wherein the variation comprises G779A, wherein the isolated nucleic acid molecule is operatively associated with a promotor. The variant human mu opioid receptor is then recovered from the host.

In another embodiment, the present invention extends to a method for producing a variant human mu opioid receptor comprising an amino acid sequence having at least two variations in SEQ ID NO:2, wherein the variations comprise Asn40Asp or conserved variants thereof;

Ala6Val or conserved variants thereof; or

Arg260His or conserved variants thereof,

Such a method comprises the steps of culturing a unicellular host transformed or transfected with an expression vector comprising a variant allele of a human mu opioid receptor gene of the present invention or an isolated nucleic acid molecule hybridizable thereto under standard hybridization conditions, and operatively associated with a promoter, that provides for expression of the variant allele or the isolated nucleic acid molecule hybridizable thereto under standard hybridization conditions. After expression, a variant human mu opioid receptor of the present invention is recovered from the unicellular host.

A wide variety of unicellular host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED PstI, SalI, SbaI, SmaI, and EcoRI cloning site, with the vector expressing both the cloned gene and DHFR; see Kaufman, Current Protocols in Molecular Biology, 16.12 (1991).

Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to produce a variant human mu opioid receptor or the present invention. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Examples of unicellular hosts contemplated by the present invention include, but are not limited to E. coli Pseudonomas, Bacillus, Strepomyces, yeast, CHO, R1.1, B-W, L-M, COS1, COS7, BSC1, BSC40, BMT10 and Sf9 cells. In addition, a host cell strain may be chosen which modulates the expression of a variant allele comprising a human mu opioid receptor gene, or an isolated nucleic acid hybridizable thereto under standard hybridization conditions, such that the gene product is modified and processed in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, a translocation signal sequence of an isolated variant allele of a human mu opioid receptor gene of the present invention, or an isolated nucleic acid hybridizable thereto under standard hybridization conditions, expressed in bacteria may not be properly spliced. Expression in yeast can produce a glycosylated product. Expression in eukaryotic cells can increase the likelihood of "native" glycosylation and folding. Moreover, expression in mammalian cells can provide a tool for reconstituting, or constituting activity of the variant human mu opioid receptor gene. Furthermore, different vector/host expression systems may affect processing reactions, such as proteolytic cleavages, to a different extent.

Vectors are introduced into the desired unicellular hosts by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartnut et al., Canadian Patent Application No. 2,012,311, filed Mar. 15, 1990).

An isolated variant human mu opioid receptor of the present invention produced as an integral membrane protein can be isolated and purified by standard methods. Generally, the variant human mu opioid receptor can be obtained by lysing the membrane with detergents, such as but not limited to, sodium dodecyl sulfate (SDS), Triton X-100, nonidet P-40 (NP-40), digoxin, sodium deoxycholate, and the like, including mixtures thereof. Solubilization can be enhanced by sonication of the suspension. Soluble forms of an isolated variant of a human mu opioid receptor can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffmity, and sizing column chromatography), centrifugation, differential solubility, immunoprecipitation, or by any other standard technique for the purification of proteins.

Due to the degeneracy of nucleotide coding sequences, other DNA sequences which encode the variant human mu opioid receptors of the present invention may be used in the practice of the present invention. These include but are not limited to allelic genes, homologous genes from other species, and nucleotide sequences comprising all or portions of genes which are altered by the substitution of different codons that encode the same amino acid residue within the sequence, thus producing a silent change. Likewise, the conserved variants of human mu opioid receptors of the present invention include, but are not limited to, those containing, as a primary amino acid sequence, substitutions of amino acids in a variant human mu opioid receptor as set forth above, which are functionally equivalent to amino acids of the variations set forth above, resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine.

The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Antibodies to Variant Human mu Opioid Receptors of the Present Invention

According to the invention, variant human mu opioid receptors disclosed herein may be used as an immunogen to generate antibodies that recognize the claimed variant mu opioid receptors. Such antibodies include but are not limited to polyclonal, monoclonal, chimeric, single chain, Fab fragments, and an Fab expression library. Furthermore, antibodies of the invention may be cross reactive, e.g., they may recognize human mu opioid receptors comprising an amino acid sequence of SEQ ID NO:1, as well as mu opioid receptors from different species. Polyclonal antibodies have greater likelihood of cross reactivity. Alternatively, an antibody of the invention may be specific for a specific variant allele of a mu opioid receptor.

Various procedures known in the art may be used for the production of polyclonal antibodies to variant opioid receptors disclosed herein. For the production of an antibody, various most animals can be immunized by injection with a variant human mu opioid receptor of the invention, including but not limited to rabbits, mice, rats, sheep, goats, etc. In one embodiment, the variant human mu opioid receptor can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward a particular human mu opioid receptor of the present invention, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for a variant human mu opioid receptor of the present invention together with genes from a human antibody molecule of appropriate biological activity can be used; such antibodies are within the scope of this invention. Such human or humanized chimeric antibodies are preferred for use in determining the presence of a particular human mu opioid receptor in a sample taken from a subject.

According to the invention, techniques described for the production of single chain antibodies [U.S. Pat. Nos. 5,476, 786 and 5,132,405 to Huston; U.S. Pat. No. 4,946,778] can be adapted to produce particular variant mu opioid receptor-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a variant mu opioid receptor of the present invention.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a variant human mu opioid receptor of the present invention, one may assay generated hybridomas for a product which binds to a fragment of the variant human mu opioid receptor containing such epitope.

The foregoing antibodies can be used in methods known in the art relating to the localization and activity of a variant human mu opioid receptor, e.g., for Western blotting, imaging a variant human mu opioid receptor in situ, measuring levels thereof in appropriate physiological samples, etc. using any of the detection techniques mentioned above or known in the art.

Yet another embodiment is based on Applicants' remarkable discovery that surprisingly, certain variant human mu opioid receptors have greater affinity for particular opioids than human mu opioid receptors comprising an amino acid sequence of SEQ ID NO:2. More specifically, Applicants have discovered that surprisingly, a variant human mu opioid receptor produced from expression of a variant allele of a human mu opioid receptor comprising a variation in SEQ ID NO:1, wherein the variation comprises A118G, binds three times more tightly to β-endorphin, an endogenous opioid comprising 31 amino acid residues, than do human mu opioid receptors produced from the expression of the predominant or "most common" allele comprising a DNA sequence of SEQ ID NO:1. Since β-endorphin is believed to play an important role in numerous physiological functions, the presence of a variant comprising A118G, in either or both alleles present in a subject has an impact on such physiological functions.

One such function involves a susceptibility to at least one addictive disease, such as opioid addiction, cocaine addiction or addiction to other psychostimulants, nicotine addiction, barbiturate or sedative hypnotic addiction, anxiolytic addiction, or alcohol addition. In particular, Applicants have discovered a variant allele of a human mu opioid receptor gene comprising a DNA sequence having at variation in SEQ ID NO:1, wherein the variation comprises A118G, is present at a statistically significant greater frequency in the genomes of persons not suffering from at least one addictive disease, relative to its presence in the genomes of persons suffering from an addictive disease, such as opioid addiction.

Moreover, Applicants have further discovered that another variant allele of a human mu opioid receptor gene comprising a DNA sequence having a variation in SEQ ID NO:1, wherein the variation comprises C17T, is present at a statistically significant greater frequency in the genomes of persons suffering from at least one addictive disease, relative to its presence in the genome of persons not suffering from at least one addictive disease.

Hence, a variant allele of a human mu opioid receptor gene comprising a DNA sequence having an A118G variation , in SEQ ID NO:1, provides resistance against susceptibility to addictive diseases, while a variant allele comprising a human mu opioid receptor having a C17T variation in SEQ ID NO:1, is expected to be indicative of increased susceptibility to at least one addictive disease.

Consequently, the present invention extends to a method for determining a susceptibility of a subject to one addictive disease comprising removing a bodily sample comprising a first and second allele of a human mu opioid receptor gene from the subject, and determining whether either the first or second alleles, or both alleles comprise a DNA sequence having at least one variation in SEQ ID NO:1, wherein the variation comprises:

A118G; or

C17T.

The presence of the variation of C17T in either or both alleles of a human mu opioid receptor gene of a sample from the subject indicates the subject has an increased susceptibility to at least one addictive disease relative to a standard having alleles of the human mu opioid receptor gene comprising a DNA sequence of SEQ ID NO:1.

Furthermore, the presence of the variation of comprising A118G, in either or both alleles of a mu opioid receptor gene in a sample from the subject is expected to indicate the subject as a decreased susceptibility to addictive diseases relative to a standard comprising alleles of a human mu opioid receptor gene comprising a DNA sequence of SEQ ID NO:1.

In this embodiment, the biological sample can be a biological fluid, such as but not limited to, blood, serum, plasma, interstitial fluid, plural effusions, urine, cerebrospinal fluid, and the like. Preferably, variant alleles of a human mu opioid receptor gene, as described above, are detected in serum or urine, which are both readily obtained. Alternatively, variant alleles of a human mu opioid receptor gene indicating increased or decrease susceptibility to addictive diseases in the subject as described above, can be detected from cellular sources, such as, but not limited to, brain tissue biopsies, adipocytes, testes, heart, and the like. For example, cells can be obtained from an individual by biopsy and lysed, e.g., by freeze-thaw cycling, or treatment with a mild cytolytic detergent such as, but not limited to, TRITON X-100®, digitonin, NONIDET P (NP)-40®, saponin, and the like, or combinations thereof (see, e.g., International Patent Publication WO 92/08981, published May 29, 1992). In yet another embodiment, samples containing both cells and body fluids can be used (see ibid.).

Other methods presently understood by a skilled artisan, and encompassed by the present invention, can also be used to detect the presence of either variation in either or both alleles of a human mu opioid receptor gene in a sample, and hence increased or decreased susceptibility to at least one addictive disease of the subject relative to the susceptibility of at least one addictive disease in a standard comprising alleles of the human mu opioid receptor gene comprising a DNA sequence of SEQ ID NO:1.

For example, an optionally detectably labeled isolated nucleic acid molecule hybridizable under standard hybridization conditions to an isolated variant allele of a human mu opioid receptor gene comprising a DNA sequence having a variation in SEQ ID NO:1, wherein the variation comprises C17T, can be used in standard Northern hybridization analysis to detect the presence, and in some instances quantitate the level of transcription of such a variant allele of the present invention. The presence of this variant allele in a bodily sample from a subject is expected to be indicative of increased susceptibility to at least one addictive disease in the subject. Likewise, an optionally detectably labeled isolated nucleic acid molecule hybridizable under standard hybridization conditions to an allele of a human mu opioid receptor gene comprising a DNA sequence having a variation in SEQ ID NO:1, wherein the variation comprises A118G can be used in a standard Northern hybridization analysis to detect the presence of a variant allele in the sample comprising a variation in SEQ ID NO:1, wherein the variation comprises A118G, which is expected to be indicative of a decreased susceptibility to at least one addictive disease relative to the susceptibility of a standard comprising two alleles of a human mu opioid receptor gene comprising a DNA sequence of SEQ ID NO:1.

Alternatively, oligonucleotides of the invention can be used as PCR primers to amplify an allele of a human mu opioid receptor gene of the biological sample e.g., by reverse transcriptase-PCR, or amplification of the allele itself. The amplified mRNA or DNA can then be quantified or sequenced in order to determine the presence of a variant allele, and the susceptibility of the subject to addictive diseases. Furthermore, variations in SEQ ID NO:1, as described above, can be found by creation or deletion of restriction fragment length polymorphisms (RFLPs) not found in the predominant or "most common" allele, hybridization with a specific probe engineered to hybridize to variation described above under standard hybridization conditions, (or lack of hybridization with a probe specific for the predominant or "most common" allele), as well as by other techniques.

Furthermore, biochemical or immunochemical/ biochemical (e.g., immunoprecipitation) techniques can be used to detect the presence and or level of expression of a variant allele of a human mu opioid receptor gene comprising a DNA sequence having a variation in SEQ ID NO:1, wherein the variation comprises:

A118G; or

C17T.

The presence of the A118G variation in either or both alleles of a human mu opioid receptor gene in a biological sample from the subject indicates a decreased susceptibility to addictive diseases in the subject, and the presence of the C17T variation in either or both alleles of a human mu opioid receptor gene in a biological sample from the subject indicates increased susceptibility to addictive diseases in the subject. For example, methods such as radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and irnmunoelectrophoresis assays, etc using antibodies of the present invention, can be used to determine the presence of a variant in an allele of a human mu opioid receptor gene in a sample taken from the subject, and hence, the subject's susceptibility to addictive diseases relative to the susceptibility of a standard. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Determining susceptibility o pain in a Subject

In yet another embodiment, the present invention extends to a method for determining a susceptibility to pain in a subject. As explained above, Applicants have discovered that endogenous opioid, such as β-endorphin, bind about three times as tightly to a variant human mu opioid receptor comprising an amino acid sequence having a in SEQ ID NO:2 wherein the variation comprises Asn40Asp, relative to the binding of β-endorphin to a human mu opioid receptor comprising an amino acid sequence of SEQ ID NO:2, encoded by the predominant or "most common" allele of a human mu opioid receptor gene comprising a DNA sequence of SEQ ID NO:1. Also, β-endorphin induced activity of a receptor produced from the expression of a variant allele of a human mu opioid receptor gene or an isolated nucleic acid molecule hybridizable thereto under standard hybridization conditions comprising the A118G polymorphism effected the receptor's activation of GIRK channels via a G protein-mediated mechanism relative to the activity of a receptor produced from the expression of the predominant or "most common" allele. Consequently, a subject having an A118G variation, in either or both alleles of a human mu opioid receptor gene is expected to have lower susceptibility and greater tolerance to pain relative to a person comprising two copies of the predominant or "most common" allele.

Applicants have further discovered a variant allele of a human mu opioid receptor gene comprising a DNA sequence having a variation in SEQ ID NO:1, wherein the variation comprises C17T, is present at a statistically significantly greater frequency in the genomes of opioid addicts relative to its presence in the genomes of persons not addicted to opioids. Hence, the presence of a variant allele of a human mu opioid receptor comprising a DNA sequence having a variation in SEQ ID NO:1, wherein the variation comprises C17T, in a biological sample taken from a subject, indicates the subject is predicted to have increased susceptibility and decreased tolerance to pain.

Hence, disclosed herein is a method of determining susceptibility of pain in a subject, comprising the steps of removing a bodily sample comprising a first and second allele of a human mu opioid receptor gene from the subject, and determining whether either the first or second alleles, or both alleles, comprise a DNA sequence having at least one variation in SEQ ID NO:1, wherein the variation comprises:

A118G; or

C17T.

The presence of at least one variation in either or both alleles of the human mu opioid receptor gene is expected to be indicative of the subject's increased or decreased susceptibility to pain relative to a person homozygous with respect to the predominant or "most common" allele comprising a human mu opioid receptor gene comprising a DNA sequence of SEQ ID NO:1.

Numerous methods presently available, and understood by the skilled artisan, can be used to "genotype" a subject in regards to the presence of a variant allele of a human mu opioid receptor gene in the genome of the subject. In particular, methods described above to ascertain increased or decreased susceptibility to addictive diseases have relevance in this embodiment of the present invention, and can readily be used herein. For example, Northern blot hybridization an isolated nucleic acid of the present invention hybridizable under standard hybridization conditions to an isolated variant allele of a human mu opioid receptor gene comprising a DNA sequence having a variation of SEQ ID NO:1, wherein the variation comprises:

A118G; or

C17T, as a probe, along with RT-PCR, PCR, and numerous immunoassays described above, have applications herein.

Moreover, once susceptibility to pain in a subject has been determined, it is possible for attending medical professionals treating the subject for pain to administer an appropriate amount of pain reliever to the subject in order to induce analgesia. More specifically, an inappropriate amount of pain reliever is administered when either the subject is not relieved of pain, or the subject is exposed to potential deleterious side effects of the pain reliever, such as induction of addiction to the pain reliever, brain damage, or death.

However, since the amount of pain reliever administered to a subject is presently based principally on weight, information regarding the genotype of the subject with respect to the human mu opioid receptor gene can help increase accuracy in determining a therapeutically effective amount of pain reliever to administer in order to induce analgesia, making the use of pain relievers much safer for the subject.

Similarly, once ascertained, a susceptibility to addiction and response to human mu opioid receptor directed therapeutic agents, appropriate medications and dosages thereof can be determined for treatment of addictive diseases.

Diagnosing and treating a disease or disorder related to a physiological function regulated by the HPA or HPG axes In yet another embodiment, the present invention extends to a method for diagnosing a disease or disorder related to a physiological function regulated by the HPA or HPG axes. Examples of such physiological functions include sexual or reproductive functions, gastrointestinal motility, immune response, or ability to withstand stress. Moreover, examples of diseases or disorders which can be diagnosed with the present invention include infertility, constipation, diarrhea, and decreased immune response to name only a few.

As explained above, Applicants have discovered that endogenous opioid, such as β-endorphin, bind about three times as tightly to a variant human mu opioid receptor comprising an amino acid sequence having a in SEQ ID NO:2 wherein the variation comprises Asn40Asp, relative to the binding of β-endorphin to a human mu opioid receptor comprising an amino acid sequence of SEQ ID NO:2, encoded by the predominant or "most common" allele of a human mu opioid receptor gene comprising a DNA sequence of SEQ ID NO:1. Also, β-endorphin induced activity of a receptor produced from the expression of a variant allele of a human mu opioid receptor gene or an isolated nucleic acid molecule hybridizable thereto under standard hybridization conditions comprising the A118G polymorphism effected the receptor's activation of GIRK channels via a G proteinmediated mechanism relative to the activity of a receptor produced from the expression of the predominant or "most common" allele. Consequently, a subject having an A118G variation, in either or both alleles of a human mu opioid receptor gene is expected to have has increased activity of the receptor relative to the activity of a receptor produced from expression of the predominant or "most common" allele comprising a DNA sequence of SEQ ID NO:1. This increased activity is expected to result in lower activity of the HPA and HPG axes. As a result sexual and reproductive functions, gastrointestinal motility, immune response and/or ability to withstand stress are increased in the subject relative to the levels of such functions in a standard comprising two alleles of the mu opioid receptor gene comprising a DNA sequence of SEQ ID NO:1.

In contrast, Applicants have discovered a human mu opioid receptor produced from expression of the C17T variant allele of the human mu opioid receptor gene is expected to have decreased binding affinity for β-endorphin relative to the binding affinity of a human mu opioid receptor protein produced from the expression of the predominant or "most common" allele of the human mu opioid receptor gene (SEQ ID NO:1) comprising a DNA sequence of SEQ ID NO:1. Consequently, a variant receptor encoded by a C17T variant allele exhibits decreased activity relative to the predominant or "most common" allele. This decreased activity results in increased activity of HPA and HPG axes. Hence, sexual and reproductive functions, gastrointestinal motility, immune response and/or ability to withstand stress are decreased in the subject relative to the levels of such physiological functions in a standard comprising two alleles of the mu opioid receptor gene comprising a DNA sequence of SEQ ID NO:1.

Hence, disclosed herein is a method of diagnosing a disease or disorder related to a physiological function regulated by the HPA or HPG axes in a subject, comprising the steps of removing a bodily sample comprising a first and second allele of a human mu opioid receptor gene from the subject, and determining whether either the first or second alleles, or both alleles, comprise a DNA sequence having at least one variation in SEQ ID NO:1, wherein the variation comprises:

A118G; or

C17T.

The presence of at least one variation in either or both alleles of the human mu opioid receptor gene is expected to be indicative of a disease or disorder related to a physiological functon regulated by the HPA or HPG axes relative to such functions in a person homozygous with respect to the predominant or "most common" allele comprising a human mu opioid receptor gene comprising a DNA sequence of SEQ ID NO:1. Examples of such physiological functions include sexual or reproductive functions, gastrointestinal motility, immune response, or ability to withstand stress. Moreover, examples of diseases or disorders which can be diagnosed with the present invention include infertility, constipation, diarrhea, and decreased immune response to name only a few, relative to a person homozygous with respect to the predominant or "most common" allele comprising a human mu opioid receptor gene comprising a DNA sequence of SEQ ID NO:1.

Numerous methods presently available, and understood by the skilled artisan, can be used to "genotype" a subject in regards to the presence of a variant allele of a human mu opioid receptor gene in the genome of the subject. In particular, methods described above to ascertain increased or decreased susceptibility to addictive diseases have relevance in this embodiment of the present invention, and can readily be used herein. For example, Northern blot hybridization an isolated nucleic acid of the present invention hybridizable under standard hybridization conditions to an isolated variant allele of a human mu opioid receptor gene comprising a DNA sequence having a variation of SEQ ID NO:1, wherein the variation comprises:

A118G; or

C17T, as a probe, along with RT-PCR, PCR, and numerous immunoassays described above, have applications herein.

In an alternative, such a method comprises removing a bodily sample from the subject comprising a mu opioid receptor, and determining whether the receptor comprises an amino acid sequence having a variation in SEQ ID NO:1, wherein the variation comprises:

Asn40Asp or conserved variants thereof; or

Ala6Val or conserved variants thereof, such that the presence of at least one variation is expected to be indicative of a disease or disorder related to a physiological function regulated by the HPA or HPG axes, such as sexual function or development, gastric motility, immune response, or the ability of the subject to withstand stress, relative to regulation of such activities in a standard comprises a human mu opioid receptor having an amino acid sequence of SEQ ID NO:2.

In particular, the presence of a variant human mu opioid receptor comprising an amino acid sequence having at least one variation in SEQ ID NO:2 wherein the variation comprises Asn40Asp or conserved variants thereof, is expected to be indicative of increased sexual or reproductive functions, increased gastrointestinal motility, increased immune response, or increased ability to withstand stress relative to the levels of such function observed in a standard having a mu opioid receptor comprising an amino acid sequence of SEQ ID NO:2.

Furthermore, the presence of a variant human mu opioid receptor comprising an amino acid sequence having a variation in SEQ ID NO:2, wherein the variation comprises Ala6Val or conserved variants thereof, in a bodily sample taken from a subject is expected to be indicative of decreased sexual or reproductive functions, decreased gastrointestinal motility, decreased immune response, or decreased ability to withstand stress relative to the levels of such function observed in a standard having a mu opioid receptor comprising an amino acid sequence of SEQ ID NO:2. Examples of specific diseases or disorders related to regulation of physiological functions regulated by the HPA or HPG axes include infertility, constipation, diarrhea, decreased immune response to antigens, or a lack of ability to withstand stress.

Numerous methods of detecting a variant mu opioid receptor as described above are presently available to the skilled artisan. For example a receptor in the bodily sample can be digested into fragments with proteases or CNBr. These fragments can then be collected and sequenced using presently known methods. Once the sequence of the receptor has been determined, it is a simple matter of comparing it to the amino acid sequence of the predominant or "most common" receptor having an amino acid sequence of SEQ ID NO:2, to determine whether a variation in the amino acid sequence exists. Other methods involve immune assays described herein using antibodies of the present invention, or a binding assay to determine the binding affinity of the receptor to β-endorphin. If its binding to β-endorphin is approximately 3 times greater than the known binding affinity of the predominant or "most common" receptor for β-endorphin, then the receptor is expected to have an amino acid sequence having a variation in SEQ ID NO:2, wherein the variation comprises Asn40Asp or conserved variants thereof, and is expected to be indicative of a disease or disorder related to increased sexual or reproductive functions, increased gastrointestinal motility, increased immune response, or increased ability to withstand stress.

Moreover, once a disease or disorder related to a physiological condition regulated by the HPA or HPG axes has been diagnosed, it is possible for attending medical professionals treating the suspect to select an appropriate therapeutic agent for treating such a disease and disorder, and a therapeutically effective amount of such pain reliever to administer to the subject. Hence naturally, the present invention extends to a method for selecting an appropriate therapeutic agent for treating a disease or disorder related to a physiological function regulated by the HPA and HPG axes, wherein such physiological functions include sexual and reproductive functions, gastrointestinal motility, immune response, and ability to withstand stress. Furthermore, diseases or disorders related to such functions which can be diagnosed with the present invention include, but are not limited to, infertility, constipation, diarrhea, and decreased immune response, to name only a few.

Commercial Kits

Furthermore, as explained above, the present invention extends to commercial kits having applications in screening a bodily sample taken from a subject for the presence of a variant allele comprising a human mu opioid receptor comprising a DNA sequence having a variation in SEQ ID NO:1, wherein the variation comprises:

A118G;

C17T.

With information obtained from the use of a test kit of the present invention, an attending health profession can determine whether the subject has an susceptibility to pain relative to a standard, an increased susceptibility to at least one addictive disease relative to the susceptibility of a standard, a therapeutically effective amount of pain reliever to administer to the subject suffering from pain in order to induce analgesia in the subject relative to the therapeutically effective amount of pain reliever to administer to a standard in order to induce analgesia in the standard, or a therapeutically effective amount therapeutic agent to administer to a subject suffering from at least one addictive disease, relative to the therapeutically effective amount of therapeutic agent to administer to standard suffering from at least one addictive disease. Furthermore, such information can also be used to diagnose a disease or disorder related to a physiological function regulated by the HPA or HPG axes, such as sexual or reproductive functions, gastrointestinal motility, immune response, or ability to withstand stress, or selecting an appropriate therapeutic agent and a therapeutically effective amount of such an agent to administer to a subject suffering from a disease or disorder related to a physiological function regulated by the HPA or HPG axes. In each use described above, the standard comprises a first and or second allele of a human mu opioid receptor gene comprising a DNA sequence of SEQ ID NO:1.

Accordingly, a test kit of the present invention for determining whether a subject comprises a variant allele of a human mu opioid receptor gene comprising a DNA sequence having a variation in SEQ ID NO:1, comprises means for detecting the presence of a variation in a first and or second allele comprising a human mu opioid receptor in a biological sample from a subject, and optimally packaged with directions for use of the kit. In one particular aspect, the means for detecting the presence of a variant allele of a human mu opioid receptor gene comprising a DNA sequence having a variation in SEQ ID NO:1, comprises a specific binding partner of a human mu opioid receptor, such as an antibody, and means for detecting the level of binding of the specific binding partner of the antibody to the particular human mu opioid receptor. In another embodiment, a test kit comprises an oligonucleotide probe for binding to a variant allele of a human mu opioid receptor gene comprising a DNA sequence having a variation in SEQ ID NO:1; and means for detecting the level of binding of the probe to the variant allele, wherein detection binding of the probe to the variant allele indicates the presence of a variant comprising a human mu opioid receptor gene comprising a DNA sequence having a variation in SEQ ID NO:1, wherein the variation comprises:

A118G; or

C17T.

The sequence of the oligonucleotide probe used in a commercial kit will determine which if any variation is present in an allele comprising a human mu opioid receptor gene. Should no binding be detected, it is probable that no such variation exists in either allele of the subject.

More specifically, a commercial test kit of the present invention comprises:

a) PCR oligonucleotide primers suitable for detection of a variant allele of a human mu opioid receptor gene comprising a DNA sequence having a variation in SEQ ID NO:1, as set forth above, b) other reagents; and c) directions for use of the kit.

Examples of PCR oligonucleotide primer suitable for detection of an allele comprising a human mu opioid receptor gene comprising a DNA sequence having a variation in SEQ ID NO:1 can be readily produced by a person of ordinary skill in the art with teaching set forth herein, and variations of SEQ ID NO:1 also set forth herein.

The present invention further extends to commercial test kits capable of detecting a variant human mu opioid receptor in a bodily sample taken from a subject. Examples of variant human mu opioid receptors that can be detected with a kit of the present invention comprise:

a variant human mu opioid receptor comprising an amino acid sequence having a variation in SEQ ID NO:2, wherein the variation comprises the variation comprises Arg260His or conserved variants thereof; or a variant human mu opioid receptor comprising an amino acid sequence having at least two variations in SEQ ID NO:2, wherein the variations comprise:

Asn40Asp or conserved variants thereof;

Ala6Val or conserved variants thereof; or

Arg260His or conserved variants thereof.

Moreover, a commercial test kit of the present invention can be used to determine: a susceptibility to pain in a subject relative to a standard, an increased susceptibility to at least one addictive disease in a subject relative to the susceptibility of a standard, a therapeutically effective amount of pain reliever to administer to the subject suffering from pain in order to induce analgesia in the subject relative to the therapeutically effective amount of pain reliever to administer to a standard in order to induce analgesia in the standard, a therapeutically effective amount of a therapeutic agent to administer to a subject suffering from at least one addictive disease, relative to the therapeutically effective amount of therapeutic agent to administer to standard suffering from at least one addictive disease, a diagnosis of a disease or disorder related to a physiological function regulated by the HPA or HPG axes, such as sexual or reproductive functions, gastrointestinal motility, immune response, or ability to withstand stress, or selecting an appropriate therapeutic agent and a therapeutically effective amount of such an agent to administer to a subject suffering from a disease or disorder related to a physiological function regulated by the HPA or HPG axes. In each use described above, the standard comprises a first and or second allele of a human mu opioid receptor gene comprising a DNA sequence of SEQ ID NO:1.

Accordingly, the present invention extends to a commercial test kit having applications set forth above, comprising a predetermined amount of at least one detectably labeled immunochemically reactive component having affinity for a variant human mu opioid receptor;

(b) other reagents; and (c) directions for use of the kit.

Antibodies of the present invention, and set forth above, have readily applications in a commercial test kit of the present invention.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the human mu opioid receptor of a bodily sample to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the human mu opioid receptor gene of the present invention and a specific binding partner thereto.

The present invention may be better understood by reference to the following non-limiting Example, which is provided as exemplary of the invention. The following Example is presented in order to more fully illustrate the preferred embodiments of the invention. It should in no way be construed, however, as limiting the broad scope of the invention.

EXAMPLE

The mu opioid receptor is the major target for clinically important opioid alkaloids including morphine, methadone, fenanyl, and other opioid drugs (1,3), as well as for endogenous opioid peptides such β-endorphin, Met-enkephalin-Arg-Phe, and the recently identified endomorphins (5). Furthermore, it is the major molecular site of action for heroin (2,6). Rapid activation of the mu opioid receptor, such as occurs in the setting of drug abuse, results in a euphoric effect, thus conferring the reinforcing or rewarding effects of the drug, contributing to the development of addiction. Clinical observations have suggested that individuals have varied sensitivity to opioids, suggesting potential variability in the receptor protein and gene.

Molecular cloning of the mu opioid receptor (7–9) has made it possible to determine potential sequence polymorphism, as shown by a recent study (10). To further identify SNPs of the mu opioid receptor, a PCR-based strategy was used to amplify the coding regions of the mu opioid receptor gene, and to determine the DNA sequence of the amplified exons. Using this method DNA samples were sequenced from 152 subjects including both former heroin addicts in methadone maintenance treatment and individuals with no history of opiate or non-opiate drug dependence.

RESULTS AND DISCUSSION

Recent studies have shown that up to 90% of persons entering treatment for heroin addiction also abuse cocaine, alcohol or other drugs. However, following stabilization on methadone maintenance pharmacotherapy (treatment for one year or more), the percentage of patients who continue to abuse cocaine drops to approximately 30% and alcohol to 25 to 30% (11–13). Rigorous characterization of substance abuse profiles was therefore obtained for all study subjects. Self reported drug abuse history was confirmed for addictive disease patients by routine urine toxicology. Also, since 20% to 50% of persons with chemical dependency may have a definable mental disorder which can be characterized by standard diagnostic criteria and also since a similarly high percentage of persons with a diagnosed mental illness have chemical dependency, extensive psychological and psychiatric evaluations of study subjects were performed (14,15).

Inclusion criteria were met by 152 individuals (refer to Methods for details of inclusion/exclusion criteria). One hundred thirteen of the study subjects (74.3%) were opiate dependent with or without previous or current co-dependency for other substances; 39 study subjects (25.7%) had no history of drug dependence. Study subjects were well balanced between females and males: 69 females (45.4%) and 83 males (56.4%) were included in the study subject pool. The ethnic breakdown of the study subject populations was as follows: African-American 31, (20.3%), Caucasian, 52 (34.2%), Hispanic, 67 (44.1%), Native North-American, 1, (0.7%) and Other, 1 (0.7%). Although several individuals could be classified into two separate groups if one parent came from one ethnic group and the other parent from another group, including four individuals (2.6%) who reported one parent African-American and one Caucasian, and five individuals (3.3%) who reported one parent Caucasian and one Hispanic, for the genotype calculations the former were classified as African-American and the latter as Hispanic. Within the group of former heroin addicts in methadone maintenance treatment, the mean years in treatment was 6.7 with a range from two months to 30 years (N=112, one patient's history could not be verified). Prior to treatment, the mean years of heroin addiction was 10.1 years, with a range from one to 30 years (N=109, four patients' histories could not be verified). The mean daily methadone dose of opiate dependent patients in stable treatment was 84 mg/day, with a range from 30 to 120 mg/day (N=106). Only patients with established stable doses were included in this calculation; i.e., not on induction, increasing, tapering, or elimination schedules.

By sequencing PCR-amplified DNA from the study subjects, it was determined that the previously reported sequence for the human mu opioid receptor (8,9) was the most common allele found in the study population. Five different SNPs were also identified. For the purpose of this study, the term "most common" was used to denote the predominant mu opioid receptor allele and the corresponding receptor that was originally reported by cDNA cloning (8,9), and the term "variant" to denote the allelic genes/receptors containing polymorphic variations. Table 1 shows these SNPs with information on the position of amino acid substitutions and overall frequency of the variant alleles in the study population. Genotype and allele frequencies for the two most common allelic variants, the A118G and C17T polymorphisms, are shown in Table 2. The associations of each frequency are broken down by ethnicity, gender, and opioid dependence. Since the number of individuals homozygous for the less common alleles was small, allele frequencies rather than genotype frequencies were used to test for significant differences. Differences of allele frequencies were tested among the three most common ethnic groups, African-American, Caucasian, and Hispanic, irrespective of opioid dependency status. There was significant difference of allele frequencies among ethnic groups for both the A118G [$\chi^2_{(2)}$=7.15 (p=0.028)] and the C17T [$\chi^2_{(2)}$=26.0 (p=0.000002)]. If the individuals who reported one parent from one ethnic group and one from another ethnic group were excluded from this analysis, similar significance levels were obtained for differences of both SNPs among ethnic groups. This result is not surprising since allele frequencies are known to vary among ethnic groups. It is important to consider these differences which can confound association analyses. No significant association of gender with either polymorphism was observed. For the A118G polymorphism, there was no significant difference in allele frequencies between opioid dependent and non-dependent study subjects. However, the variant T allele at the 17 position was present in a higher proportion of opiate dependent persons in the sample at a marginal significance level [Yates corrected chi-square $\chi^2_{(1)}$=3.70 (p=0.054).

This result is similar to that obtained in a previous study which identified this one SNP, and examined its frequency in association with drug dependence (10). Table 3 shows the data stratified by ethnic group and opiate dependency status for each of the A118G and C17T polymorphisms. The pooled Relative Risk (RR) and the Mantel-Haenszel chi-square (16) were calculated. For the A118G polymorphism there was no significant difference in allele frequencies between opioid dependent persons and those with no history of drug abuse or dependence [RR=0.48 $\chi^2_{(1)}$=2.76 (p=0.096)]. Although not significant there was evidence of heterogeneity between ethnic groups [RR=0.48 $\chi^2_{(2)}$=5.16 (p=0.076)]. It should be noted that the direction of the Relative Risk less than one denotes here that the A118G polymorphism was more frequent in normal healthy volunteers with no history of drug dependence (controls) than opioid dependent subjects (cases), and if present, the A118G polymorphism might confer some level of protection against opioid dependence, which is of particular interest given the functional differences (see below). There was a marginally significant difference in the allele frequencies for the C17T polymorphism between cases and controls [RR=7.83 $\chi^2_{(1)}$=3.73 (p=0.05)]. The test for heterogeneity among ethnic groups was not significant [$\chi^2_{(2)}$=3.95 (p=0.14)].

Cases and controls were examined for Hardy Weinberg equilibrium (HWE) by each ethnic group individually and for all ethnic groups combined. All groups analyzed were in HWE, except for the C17T polymorphism for the opioid dependent subjects with all ethnic groups combined which showed significant deviation from HWE (p=0.008). Although under no obligation to provide a reason for this observation, and not intending to be bound by any postulation to explain this observation, these results may be due to the admixture introduced by combining the different ethnic groups into one sample.

The most prevalent genetic polymorphism identified is the A118G SNP with a substitution at the nucleotide position 118 with respect to the first base of the initiator codon for methionine (FIG. 1). This allele was observed in 29 of the 152 subjects, with 26 subjects being heterozygous and 3 being homozygous for the variant allele. This gives an allele frequency of 10.5% in the subject population that we have examined for this study. Nucleotide no. 118 is the first base in codon no. 40 of the human mu opioid receptor, and the A118G variant predicts an Asn to Asp change in amino acid residue no. 40 of the receptor (N40D). The Asn residue at amino acid position no. 40 in the most common mu receptor is a putative site for N-glycosylation (9); thus, the A118G variant would result in the loss of a putative N-glycosylation site. The position of amino acid 40 is in the N terminal region of the mu opioid receptor (9). Based on sequence motif similarities with other G protein-coupled receptors (17), the N terminal region of opioid receptors, including that of the mu opioid receptor, is predicted to be in the extracellular space (18). To explore any potential effects of the A118G polymorphism on the mu opioid receptor, position 118 of the most common mu receptor cDNA was mutated by site-directed mutagenesis, and a cDNA clone for the human mu opioid receptor containing the A118G variant was generated. This way, both the most common and the A118G variant receptors could be expressed in cells to determine their cellular activity and their binding affinities.

Radioligand binding assays were performed with cell lines stably transfected with either the A118G variant or the most common mu receptor, to determine whether the A118G polymorphism changes the receptor's ability to bind opioid ligands, especially endogenous opioid peptides, since they are the physiological agonists for the mu opioid receptor. The A118G variant and the most common mu receptors yielded similar binding affinity values for most of the opioid ligands tested, including the small endogenous peptide agonists Met- and Leu-enkephalin, each with five amino acid residues; endomorphin-1 and -2, each with four residues; the mu-selective synthetic opioid peptide DAMGO, with five amino acid residues; the endogenous ligand for the kappa opioid receptor dynorphin A (1–17); as well as the mu-preferring opioid alkaloid agonists morphine, fentanyl, methadone, and the opioid antagonist naloxone (FIG. 2, and data not shown). These results suggest that the A118G polymorphism does not change the overall binding properties of the mu opioid receptor. This is not unexpected, since the predicted amino acid change as a result of the A118G SNP is a single residue substitution in the N terminal region in the extracellular space, and is unlikely to drastically affect the overall tertiary structure of the receptor.

There was a noticeable change, however, for the A118G variant receptor binding of human β-endorphin, a much larger endogenous opioid peptide, which has 31 amino acid residues and which activates the mu opioid receptor. Whereas the other, smaller, endogenous opioid peptides and alkaloid agonists and antagonist displayed similar binding affinities for both receptors, the A118G variant receptor showed higher binding affinity for β-endorphin than the most common receptor (FIG. 2), with the ratio of the Ki of the most common to A118G variant being 3.46±0.31 (mean±SEM, n=3). These results indicate that while the A118G polymorphism did not alter the overall profile of ligand binding to the receptor, it specifically influenced the β-endorphin binding and resulted in tighter binding.

Figure 3A:
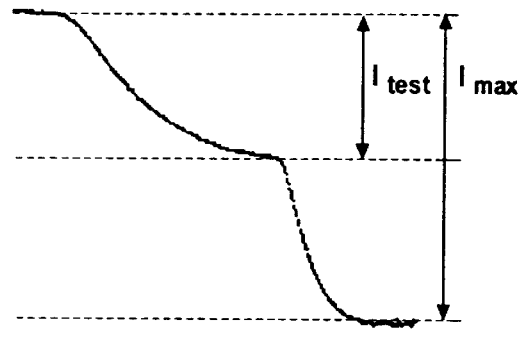
FIGS. 3A and 3B: Functional comparison of the most common (SEQ ID NO:1) and A118G variant variant human mu opioid receptors in coupling to G protein-activated inwardly rectifying K$^+$ (GIRK) channels. (A) Example of current trace showing the experimental protocol and calculation method for the agonist-induced response. Oocytes were clamped at a holding potential of −80 mV and superfused with different solutions as indicated. $I_{max}$: maximum K$^+$ currents evoked by DAMGO at a saturating concentration (100 nM). $I_{Test}$: K$^+$ currents evoked by the test dose of agonists. (B) Dose response curves of receptor activation. The tested concentrations of agonists ranged from 0.1 nM to 1 μM. The response to a test dose is expressed as the fraction of the maximum activation by 100 nM DAMGO ($I_{test}/I_{max}$). Data are presented as mean±SEM (n=4–5). All oocytes were used only once to avoid desensitization.
Figure 3B:
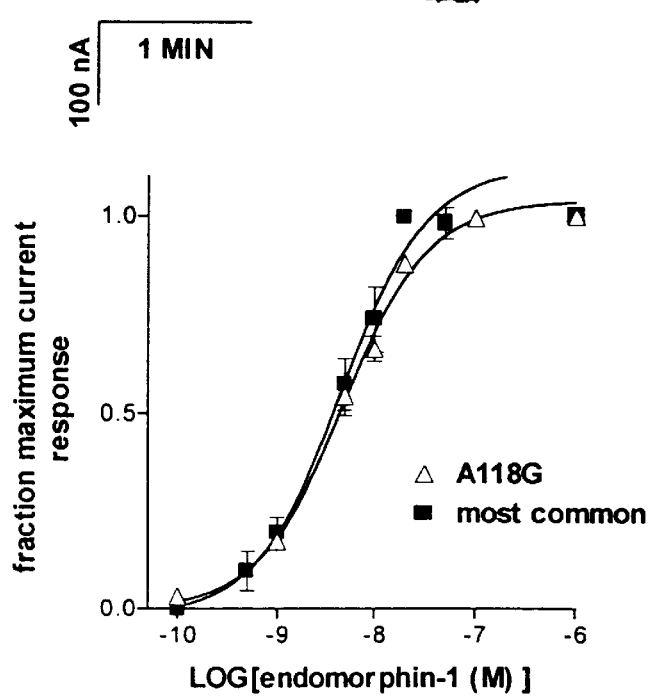
Figure 3C:
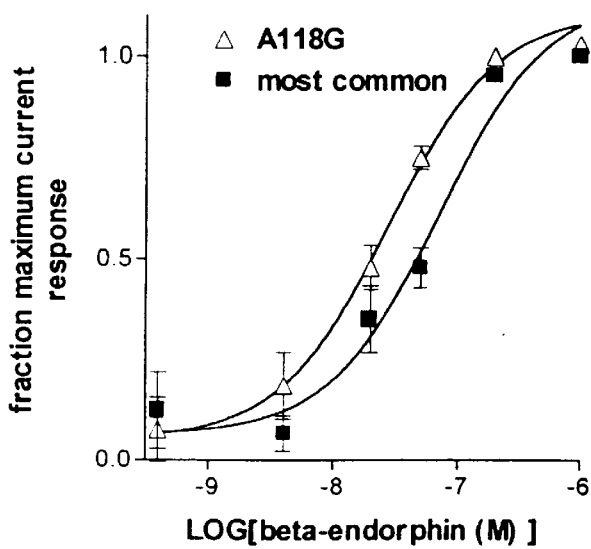

An important cellular activity of the mu opioid receptor is inhibition of neuronal excitability by receptor-mediated inhibition of pre-synaptic calcium channels and activation of post-synaptic potassium channels (19, 20). The major effector potassium channels for the mu receptor, as well as for many other G protein-coupled receptors, are the G protein-activated inwardly rectifying $K^+$ (GIRK) channels (21,22), and co-expression studies have shown that the mu opioid receptor can readily activate GIRK channels via a G protein-mediated mechanism (9,23,24). To examine the effect of the A118G polymorphism, Xenopus oocyte expression was used to compare the A118G variant receptor with the most common mu opioid receptor. Agonist stimulation of the A118G variant receptor activated a potassium current similar to that seen with the most common mu opioid receptor (9,23). The $EC_{50}$ values for endomorphin-1 are 4.6 nM for the most common receptor and 4.9 nM for the A118G variant receptor (FIG. 3), indicating that endomorphin-1 activated both receptors with similar potency. The $EC_{50}$ values for β-endorphin, however, differed about three fold between the A118G variant and the most common mu opioid receptors (FIG. 3), consistent with the change in the binding affinity (FIG. 2). These data indicate that, as a result of the SNP in the receptor gene, the A118G variant receptor may be functionally different from the most common mu opioid receptor.

An endogenous opioid with wide distribution in both the CNS and the periphery, β-endorphin has been postulated to play a role in diverse biological functions (25–27). As a neuropeptide, it can modulate neurotransmitter actions in the CNS to mediate antinociception. It is also a mediator in the stress response, of potential importance for the pathophysiology of the addictive diseases (28–36). β-endorphin can regulate the secretion of both stress and reproductive hormones, thereby influencing a variety of physiological functions. The synthesis and processing of β-endorphin is, in turn, regulated by other factors, including certain neurotransmitters and hormones. Given the diverse roles of β-endorphin, it is particularly interesting that the A118G polymorphism may change both the binding affinity and functional potency of β-endorphin. On the basis of approximately three fold difference in the affinity and potency values (FIG. 2 and 3), it is possible that two individuals with different mu opioid receptors (most common vs. A118G variant) may show variation in β-endorphin sensitivity. This, in turn, could alter perception of pain. It also could alter the vulnerability to develop opioid addiction following exposure to opiates as well as addictions to other drugs that alter the opioid system (2,6,37).

METHODS
Study subjects and procedures

Addictive disease patients, specifically long-term heroin addicts currently in chronic methadone maintenance treatment, and normal control subjects with no history of any drug or alcohol abuse, were extensively characterized with respect to drug abuse, the addictive diseases, psychological and psychiatric profiles, and medical and ethnic family backgrounds. Unrelated study subjects who were former heroin addicts were referred from methadone treatment clinics in the greater New York City area, primarily those associated with The Biology of Addictive Diseases Laboratory located at The Rockefeller University. These clinics are the Adolescent Development Program and Adult Clinic at the New York Hospital-Cornell Medical Center. Previously heroin-addicted patients admitted to the study conformed to the federally regulated criteria for admission to a methadone maintenance program, that is, one or more years of daily multiple-dose self-administration of heroin or other opiates with the development of tolerance, dependence, and drug-seeking behavior (38). Current or prior abuse of other drugs was not used as an exclusion criterion for this group as long as opioid abuse continued to be the primary diagnosis.

Unrelated healthy volunteer subjects were recruited primarily through posting of notices and newspaper advertisements or referral by physicians or staff at the Rockefeller University Hospital. Individuals with continuing drug or alcohol abuse or prior extended periods of regular abuse were excluded from this category. The exclusion criteria were defined as follows: for current or continuing abuse, alcohol, at least five (for men) or four (for women) instances of drinking to intoxication during the previous 30 days; opiates, cocaine, amphetamines, or other illicit drugs (excluding cannabis), any use during the previous 30 days. Users of nicotine or caffeine were not excluded, nor were individuals who had abused cannabis for up to 12 days during the previous 30 days. For prior abuse, subjects were excluded who had abused illicit drugs, excluding cannabis, for at least three times a week for a period of at least one month. All study subjects were rigorously screened to assure appropriate characterization of addictive diseases, status of treatment, and presence or absence of polydrug or alcohol abuse. Subjects entering the study were required to be competent to understand the study procedures and understand and sign the Institutional Review Board approved informed consent. Patients with schizophrenia or other psychotic mental illnesses were excluded from the study by this criterion. The presence of serological markers for hepatitis B, C or HIV was not used as an exclusion criterion.

Both addictive disease patients and normal volunteers admitted to the study were assessed by a psychiatrist or research nurse with several psychiatric and psychological instruments as well as the Addiction Severity Index (39). Study subjects were also administered a detailed personal and medical and special addictive disease questionnaire as well as a family history medical and addictive disease questionnaire designed to provide information regarding substance abuse and major mental illness of first and second degree relatives. Study subjects provided detailed information regarding family origin and ethnic background, including country or geographic area of birth. This information was obtained for both the study subjects themselves and their immediate ancestors (parents, grandparents and great-grandparents), to the extent that the information was known by the study subjects. Study subjects were classified into five groups: African-American, Caucasian, Hispanic (Caribbean and Central or South American origin), Native North American, and Other. The detailed ancestral information collected by the family origin questionnaire allowed classification of study subjects into defined categories. Following psychiatric and behavioral assessment and informed consent and family history acquisition, venipuncture on the study subject was performed, and a blood specimen was taken.

Blood samples were processed for DNA extraction and EBV transformation to create stable cell lines that were stored for future studies. All blood samples were coded; the psychiatrists and nurses who performed psychiatric and psychological assessments were blind to the genotypes of the study subjects, and the identity and categorization of the study subjects was unknown to the laboratory research personnel.

Exon amplification and sequencing

Sequences for the non-coding regions of the human mu opioid receptor gene were used to design PCR primers. PCR primers were synthesized for three of the four exons of the gene; the fourth exon was not included in this study because this exon is small (4 or 12 amino acid residues) and alternative splicing in this exon has been shown to occur (40). Exon 1 forward primer sequences were based on the 5'-untranslated region of the receptor (9). Exon 1 reverse, exon 2 forward and reverse, and exon 3 forward primer sequences were based on partial intron sequence data obtained from inverse PCR of genomic DNA sequences for the receptor gene (data not shown). Exon 3 reverse primers were based on reported intron 3 sequence (40). Two sets of primers were designed for each exon to allow for nested PCR reactions to increase amplification specificity. Only one reverse primer was used for exon 1. The PCR reactions were performed with 300–400 ng of genomic DNA, PCR products were separated on agarose gels, and the DNA fragments were purified for DNA sequencing. DNA polymorphisms were confirmed by both manual and automated sequencing.

Mutagenesis

In vitro site-directed mutagenesis was performed to generate human mu opioid receptor (hMOR) cDNA containing the A118G SNP. Complementary oligonucleotides containing the desired mutation were synthesized and annealed to the pcDNA3 plasmid containing the most common allelic form of HMOR.

Primer 1: TTGTCCCACTTAGATGGCGACCTGTC-CGACCCA (SEQ ID NO:6). Primer 2:

ACCGCATGGGTCGGACAGGTCGCCATCTAAGTG (SEQ ID NO:7). Primers were extended and the product amplified by PCR using HMOR dsDNA as the template, and Dpn I restriction enzyme was added afterwards to digest the methylated, nonmutated most common dsDNA. After transformation into *E. coli* cells, DNA from individual colonies was examined by restriction enzyme digestion and DNA sequencing to confirm success of mutagenesis.

Cell Transfection and Binding Analysis

Stable transfection of the A118G SNP plasmid into AV-12 cells was performed as described (41). Individual colonies were then picked, expanded, and tested for expression levels by performing binding assays. Cells were harvested by washing with phosphate-buffered saline (PBS) at room temperature, then they were scraped into homogenization solution (0.3 M sucrose, 25 mM Tris-HCl, pH 7.4, 0.05% BSA, and protease inhibitor cocktail, including 0.5 mM PMSF, 0.1 µg/ml leupeptin, and 0.01% aprotinin), transferred to Dounce homogenizer and homogenized on ice. The suspension was centrifuged at 1,000 g for 10 min and the supernatant saved in a clean tube. The cell pellet was resuspended in homogenization buffer, homogenized and centrifuged as described above. The supernatants from both extractions were combined and centrifuged at 30,000 g for 20 min. The pelleted membranes were resuspended in binding buffer (50 mM Tris-HCl, pH 7.4), and binding assays were carried out using membrane protein preparations as described (9).

Electrophysiology

Preparation of Xenopus oocytes was as previously reported (19). Oocytes were injected with in vitro transcribed mRNAs for the most common or A118G variant mu opioid receptors together with the G protein-activated inwardly rectifying $K^+$ channels (GIRK1 and GIRK2). Two to three days after RNA injection, oocytes were voltage-clamped in ND96 solution (96 mM NaCl, 2 mM KCl, 1 mM $MgCl_2$, 1.8 mM $CaCl_2$, 5 mM HEPES, pH 7.6) using a two-electrode voltage-clamp (Axon Instruments). Cells were then superfused with a high potassium solution (98 mM KCl, 1 mM $MgCl_2$, 1.8 mM $CaCl_2$, 5 mM HEPES, pH 7.6), and stimulated with opioid ligands to measure the resulting potassium current.

TABLE 1

Single nucleotide polymorphisms in the human mu opioid receptor gene. Nucleotide position I is the first base of the start codon. Protein domains are based on the 7-transmembrane model for opioid receptors. EL, extracellular loop; CL, cytoplasmic loop.

| Variant name | Nucleotide position | Exon location | Corresponding amino acid change | Protein domain | Allele frequency |
|---|---|---|---|---|---|
| A118G | 118 | 1 | Asn40Asp (N40D) | N terminal | 10.5% (26 heterozygous individuals and 3 homozygous individuals in 152 subjects examined) |
| C17T | 17 | 1 | Ala6Val (A6V) | N terminal | 6.6% (14 heterozygous individuals and 3 homozygous individuals in 152 subjects examined) |
| G24A | 24 | 1 | Silent mutation | N terminal | 2% (6 heterozygous individuals in 152 subjects examined) |
| G779A | 779 | 3 | Arg260His (R260H) | CL3 | 1 heterozygous individual |
| G942A | 942 | 3 | Silent mutation | EL3 | 1 heterozygous individual |

TABLE 2

Genotype and Allele Frequency Associations

| | A118G Genotype frequencies | | | | A118G Allele frequencies | | | C17T Genotype frequencies | | | | C17T Allele frequencies | | |
|---|---|---|---|---|---|---|---|---|---|---|---|---|---|---|
| | A/A | A/G | G/G | Total | A | G | Total | C/C | C/T | T/T | Total | C | T | Total |
| A. Ethnicity | | | | | | | | | | | | | | |
| African-American | 30 (0.968) | 1 (0.032) | 0 — | 31 | 61 (0.984) | 1 (0.016) | 62 | 21 (0.677) | 7 (0.226) | 3 (0.097) | 31 | 49 (0.790) | 13 (0.210) | 62 |
| Caucasian | 41 (0.788) | 10 (0.192) | 1 (0.019) | 52 | 92 (0.885) | 12 (0.115) | 104 | 50 (0.962) | 2 (0.038) | 0 — | 52 | 102 (0.981) | 2 (0.019) | 104 |
| Hispanic | 50 (0.746) | 15 (0.225) | 2 (0.030) | 67 | 115 (0.858) | 19 (0.142) | 134 | 62 (0.925) | 5 (0.075) | 0 — | 67 | 129 (0.963) | 5 (0.037) | 134 |
| | | | | | $\chi^2_{(2)} = 7.15$ (p = 0.028) | | | | | | | $\chi^2_{(2)} = 26.0$ (p = 0.000002) | | |
| B. Gender | | | | | | | | | | | | | | |
| Female | 59 (0.855) | 8 (0.116) | 2 (0.029) | 69 | 126 (0.913) | 12 (0.087) | 138 | 58 (0.841) | 9 (0.130) | 2 (0.029) | 69 | 125 (0.906) | 13 (0.094) | 138 |
| Male | 64 (0.771) | 18 (0.217) | 1 (0.012) | 83 | 146 (0.880) | 20 (0.120) | 166 | 77 (0.928) | 5 (0.060) | 1 (0.012) | 83 | 159 (0.958) | 7 (0.042) | 166 |
| | | | | | Yates corrected $\chi^2_{(1)} = 0.90$ (p = 0.343) | | | | | | | Yates corrected $\chi^2_{(1)} = 2.53$ (p = 0.112) | | |
| C. Opiate Dependence | | | | | | | | | | | | | | |
| Dependent | 94 (0.832) | 18 (0.159) | 1 (0.009) | 113 | 206 (0.912) | 20 (0.088) | 226 | 97 (0.858) | 13 (0.115) | 3 (0.027) | 113 | 207 (0.916) | 19 (0.084) | 226 |
| Non-dependent | 29 (0.744) | 8 (0.205) | 2 (0.051) | 39 | 66 (0.846) | 12 (0.154) | 78 | 38 (0.974) | 1 (0.026) | 0 — | 39 | 77 (0.987) | 1 (0.013) | 78 |
| | | | | | Yates corrected $\chi^2_{(1)} = 1.98$ (p = 0.159) | | | | | | | Yates corrected $\chi^2_{(1)} = 3.7$ (p = 0.054) | | |

Note: The two individuals that were not classified into African-American, Caucasian or Hispanic ethnic groups were not included in the analysis.

TABLE 3

Stratification of opioid-dependent and non-dependent study subjects by ethnicity
The two individuals that were not classified into African-American, Caucasian or Hispanic ethnic groups were not included in the analysis.

| | Position 118 | | | | Position 17 | | | |
|---|---|---|---|---|---|---|---|---|
| | Opioid Dependent (Cases) | | Non-Opioid Dependent (Control) | | Opioid Dependent (Cases) | | Non-Opioid Dependent (Control) | |
| | A | G | A | G | C | T | C | T |
| African-American | 45 | 1 | 16 | 0 | 33 | 13 | 16 | 0 |
| Caucasian | 53 | 7 | 39 | 5 | 59 | 1 | 43 | 1 |
| Hispanic | 104 | 12 | 11 | 7 | 111 | 5 | 18 | 0 |
| Combined | 202 | 20 | 66 | 12 | 203 | 19 | 77 | 1 |

References

1. Reisine, T. & Pasternak, G. W. (1996) in *Goodman & Gilman's The Pharmacological Basis of Therapeutics*, (eds. Hardman, J. G., Limbird, L. E., Molinoff, P. B., Ruddon, R. W. & Gilman, A. G.) 9th ed., 521–554 McGraw-Hill, New York, 1996.
2. Kreek, M. J. Opiates, opioids and addiction. *Mol. Psychiatry* 1, 232–254 (1996).
3. Pasternak, G. W. Pharmacological Methanisms of opioid analgesics. *Clin. Neuropharmacol.* 16, 1–18 (1993).
4. Yu, L. In *Encyclopedia of Human Biology* (ed Dulbecco, R.) 2nd ed., 445–450 Academic Press, (1997).
5. Zadina, J. E., Hackler, L., Ge, L. J., & Kastin, A. J. A potent and selective endogenous agonist for the mu-opiate receptor. *Nature* 386, 499–502 (1997).
6. Kreek, M. J. Opioid receptors: some perspectives from early studies of their role in normal physiology, stress responsivity, and in specific addictive diseases. *Neurochem. Res.* 21, 1469–1488 (1996).
7. Chen, Y., Mestek, A., Liu, J., Hurley, J. A. & Yu, L. Molecular cloning and functional expression of a mu-opioid receptor from rat brain. *Mol. Pharmacol.* 44, 8–12 (1996).
8. Wang, J. B., Johnson, P. S., Persico, A. M., Hawkins, A. L., Griffin, C. A. & Uhl, G. R. Human mu opioid receptor: cDNA and genomic clones, pharmacologic characterization and chromosomal assigrnent. *FEBS Lett.* 338, 217–222 (1994).
9. Mestak, A., Hurley, J. H., Bye, L. S., et al. The human mu opioid receptor: Modulation of functional desensitization by calcium/calmodulin-dependent protein kinase and protein kinase C. *J. Neurosci.* 15, 2396–2406 (1995).
10. Berrettini, W. H., Hoehe, M. R., Ferrada, T. N. & Gottheil, E. (1997) *Addiction Biol.* 2, 303–308.
11. Kreek, M. J. Medical complications in methadone patients. *Ann. N. Y. Acad. Sci.*, 311, 110–134 (1978).
12. Kreek, M. J. Using methadone effectively: achieving goals by application of laboratory, clinical, and evaluation research and development of innovative programs. *NIDA Res. Monograph*, 106, 245–266 (1991).
13. Borg, L., Broe, D. M., Ho, A. & Kreek, M. J. in *Problems of Drug Dependence 1994: Proceedings of the 56th Annual Scientific Meeting of the College on Problems of Drug Dependence* (ed Harris, L. S.) 17 (1995).
14. Woody, G. E., McLellan, A. T., Luborsky, L., O'Brien, C. P., Blaine, J., Fox, S., Herman, I. & Beck, A. T. (1984) *Am. J. Psychiatry* 141, 1172–1177.
15. Mason, B., Kreek, M. J., Kocsis, J., Melia, D. & Sweeney, J. (1992) in *Problems of Drug Dependence 1991: Proceeding of the 53rd Annual Scientific Meeting of the College on Problems of Drug Dependence*, ed. Harris, L. S. 230.
16. Mantel, N. & Haenszel, W. (1959) *J. Natl. Cancer Inst.* 22, 719–748.
17. O'Dowd, B. F., Lefkowitz, R. J. & Caron, M. G. (1989) *Ann. Rev. Neurosci.* 12, 67–83.
18. Chen, Y., Mestek, A., Liu, J. & Yu, L. (1993) *Biochem. J.* 295, 625–628.
19. North, R. A. (1993) in *Handbook of Experimental Pharmacology* (vol. 104): *Opioids I*, ed. Herz, A. (Springer-Verlag, Berlin), pp. 773–797.
20. Chavkin, C. (1988) in *The Opiate Receptors*, ed. Pasternak, G. W. (Humana Press, New Jersey), pp. 273–303.
21. Kubo, Y., Reuveny, E., Slesinger, P. A., Jan, Y. N. & Jan, L. Y. (1993) *Nature* 364, 802–806.
22. Dascal, N., Schreibmayer, W., Lim, N. F., Wang, W., Chavkin, C., DiMagno, L., Labarca, C., Kieffer, B. L., Gaveriaux-Ruff, C., Trollinger, D., Lester, H. A. & Davidson, N. (1993) *Proc. Natl. Acad. Sci. USA* 90, 10235–10239.
23. Chen, Y. & Yu, L. (1994) *J. Biol. Chem.* 269, 7839–7842.
24. Kovoor, A., Henry, D. J. & Chavkin, C. (1995) *J. Biol. Chem.* 270, 589–595.
25. Kreek, M. J. & Hartman, N. (1982) *Ann. N. Y. Acad. Sci.* 398, 151–172.
26. Herz, A. (1993) *Opioids I & II* (Springer-Verlag, Berlin).
27. Zhou, Y., Spangler, R., LaForge, K. S., Maggos, C. E., Ho, A. & Kreek, M. J. (1996) *Peptides* 17, 435–441.
28. Kreek, M. J., Wardlaw, S. L., Friedman, J., Schneider, B. & Frantz, A. G. (1981) in *Advances in Endogenous and Exogenous Opioids*, eds. Simon, E. & Takagi, H. (Kodansha Ltd. Publishers, Tokyo, Japan), pp. 364–366.
29. Kreek, M. J., Wardlaw, S. L., Hartman, N., Raghunath, J., Friedman, J., Schneider, B. & Frantz, A. G. (1983) *Life Sci.* 33 Suppl 1, 409–411.
30. Kreek, M. J., Ragunath, J., Plevy, S., Hamer, D., Schneider, B. & Hartman, N. (1984) *Neuropeptides* 5, 277–278.
31. Ragavan, V. V., Wardlaw, S. L., Kreek, M. J. & Frantz, A. G. (1983) *Neuroendocrinology* 37, 266–268.
32. Kosten, T. R., Kreek, M. J., Swift, C., Carney, M. K. & Ferdinands, L. (1987) *Life Sci.* 41, 1071–1076.
33. Kosten, T. R., Kreek, M. J., Ragunath, J. & Kleber, H. D. (1986) *Life Sci.* 39, 55–59.
34. Kennedy, J. A., Hartman, N., Sbriglio, R., Khuri, E. & Kreek, M. J. (1990) *Br. J. Addiction* 85, 1133–1140.
35. Culpepper-Morgan, J. A., Twist, D. J., Petrillo, C. R., Soda, K. M. & Kreek, M. J. (1992) *Metabolism: Clinical & Experimental* 41, 578–581.
36. Culpepper-Morgan, J. A. & Kreek, M. J. (1997) *Metabolism: Clinical & Experimental* 46, 130–134.
37. Kreek, M. J. (1997) *Pharmacol. Biochem. Behav.* 57, 551–569.
39. McLellan, A. T., Luborsky, L., Woody, G. E. & O'Brien, C. P. (1980) *J. Nerv. Ment. Dis.* 168, 26–33.
40. Bare, L. A., Mansson, E. & Yang, D. (1994) *FEBS Lett.* 354, 213–216.
41. Chen, Y., Liu, J. & Yu, L. (1996) *Addiction Biol.* 1, 49–59.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated variant allele of a human mu opioid receptor gene, comprising a DNA sequence having a variation in SEQ ID NO:1, wherein said variation comprises:
G24A; or
G942A,
or combinations thereof.

2. The isolated variant allele of claim 1, detectably labeled.

3. The isolated variant allele of claim 2, wherein said detectable label comprises a radioactive element, a chemical which fluoresces, or an enzyme.

4. A cloning vector comprising an isolated variant allele of a human mu opioid receptor gene and an origin of replication, wherein said variant allele comprises a DNA sequence having a variation in SEQ ID NO:1, wherein said variation comprises:
G24A; or
G942A,
or combinations thereof.

5. The cloning vector of either of claim 4, wherein said cloning vector comprises of E. coli, bacteriophages, plasmids, or pUC plasmid derivatives.

6. The cloning vector of claim 5, wherein bacteriophages further comprise lambda derivatives, plasmids further comprise pBR322 derivatives, and pUC plasmid derivatives further comprise pGEX vectors, or pmal-c, pFLAG.

7. An expression vector comprising an isolated variant allele of a human mu opioid receptor gene comprising a DNA sequence having a variation in SEQ ID NO:1, wherein said variation comprises:
G24A; or
G942A,
or combinations thereof.

8. The expression vector of claim 7, wherein said promoter comprises immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor.

9. A unicellular host transformed or transfected with an expression vector comprising an isolated variant allele of a human mu opioid receptor gene operatively associated with a promoter, wherein said variant allele comprises a DNA sequence having at least one variation in SEQ ID NO:1, wherein said at least one variation comprises:

G24A; or

G942A, or combinations thereof.

10. The unicellular host of claim 9, wherein said host comprises E. coli, Pseudonomas, Bacillus, Strepomyces, yeast, CHO, R1.1, B-W, L-M, COS1, COS7, BSC1, BSC40, BMT10 or Sf9 cells.

11. An isolated variant allele of a human mu opioid receptor gene, wherein said variant allele comprises a DNA sequence having at least two variations in SEQ ID NO:1, one of which is G24A, or G942A, wherein said variations comprise:

A118G;

C17T;

G24A; or

G942A.

12. The isolated variant allele of claim 11, detectably labeled.

13. The isolated variant allele of claim 12, wherein said detectable label comprises a radioactive element, a chemical which fluoresces, or an enzyme.

14. A cloning vector comprising an isolated variant allele of a human mu opioid receptor gene and an origin of replication, wherein said variant allele comprises a DNA sequence having at least two variations in SEQ ID NO:1, one of which is G24A, or G942A, wherein said variations comprise:

A118G;

C17T;

G24A; or

G942A.

15. The cloning vector of claim 14, wherein said cloning vector comprises E. coli, bacteriophages, plasmids, or pUC plasmid derivatives.

16. The cloning vector of claim 15, wherein bacteriophages further comprise lambda derivatives, plasmids further comprise pBR322 derivatives, pUC plasmid derivatives further comprise pGEX vectors, or pmal-c, pFLAG.

17. An expression vector comprising an isolated variant allele of a human mu opioid receptor gene operatively associated with a promoter, wherein said variant allele comprises a DNA sequence having at least two variations in SEQ ID NO:1, one of which is G24A, or G942A, wherein said variations comprise:

A118G;

C17T;

G24A; or

G942A.

18. The expression vector of claim 17, wherein said promoter comprises immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the trp system, the TAC system, the TRC system, the major operator and promoter regions of phage lambda, control regions of fd coat protein, 3-phosphoglycerate kinase promoter, acid phosphatase promoter, or promoters of yeast α mating factor.

19. A unicellular host transformed with an expression vector of claim 17.

20. A unicellular host transformed with an expression vector of claim 17.

21. The unicellular host of either of claims 19 or 20, wherein said host comprises E. coli, Pseudonomas, Bacillus, Strepomyces, yeast, CHO, R1.1, B-W, L-M, COS1, COS7, BSC1, BSC40, BMT10 or Sf9 cells.

* * * * *

SEQUENCE LISTING

```
<160> NUMBER OF SEQ ID NOS: 7

<210> SEQ ID NO 1
<211> LENGTH: 2162
<212> TYPE: DNA
<213> ORGANISM: Homo sapiens
<220> FEATURE:
<221> NAME/KEY: misc_feature
<222> LOCATION: (2063)
<223> OTHER INFORMATION: No feature for this position in GeneBank.
<220> FEATURE:
<221> NAME/KEY: misc_feature
<222> LOCATION: (2091)
<223> OTHER INFORMATION: No feature for this position in GeneBank.

<400> SEQUENCE: 1
ggaattccgg ctataggcag aggagaatgt cagatgctca gctcggtccc ctccgcctga    60
cgctcctctc tgtctcagcc aggactggtt tctgtaagaa acagcaggag ctgtggcagc   120
ggcgaaagga agcggctgag gcgcttggaa cccgaaaagt ctcggtgctc ctggctacct   180
cgcacagcgg tgcccgcccg gccgtcagta ccatggacag cagcgctgcc cccacgaacg   240
ccagcaattg cactgatgcc ttggcgtact caagttgctc cccagcaccc agccccggtt   300
cctgggtcaa cttgtccac ttagatggca acctgtccga cccatgcggt ccgaaccgca   360
ccaacctggg cgggagagac agcctgtgcc ctccgaccgg cagtccctcc atgatcacgg   420
ccatcacgat catggccctc tactccatcg tgtgcgtggt ggggctcttc ggaaacttcc   480
tggtcatgta tgtgattgtc agatacacca agatgaagac tgccaccaac atctacattt   540
tcaaccttgc tctggcagat gccttagcca ccagtacccct gcccttccag agtgtgaatt   600
acctaatggg aacatggcca tttggaacca tccttttgcaa gatagtgatc tccatagatt   660
actataacat gttcaccagc atattcaccc tctgcaccat gagtgttgat cgatacattg   720
cagtctgcca ccctgtcaag gccttagatt tccgtactcc ccgaaatgcc aaaattatca   780
atgtctgcaa ctggatcctc tcttcagcca ttggtcttcc tgtaatgttc atggctacaa   840
caaaatacag gcaaggttcc atagattgta cactaacatt ctctcatcca acctggtact   900
gggaaaacct cgtgaagatc tgtgttttca tcttcgcctt cattatgcca gtgctcatca   960
ttaccgtgtg ctatggactg atgatcttgc gcctcaagag tgtccgcatg ctctctggct  1020
ccaaagaaaa ggacaggaat cttcgaagga tcaccaggat ggtgctggtg gtggtggctg  1080
tgttcatcgt ctgctggact cccattcaca tttacgtcat cattaaagcc ttggttacaa  1140
tcccagaaac tacgttccag actgtttctt ggcacttctg cattgctcta ggttacacaa  1200
acagctgcct caacccagtc ctttatgcat ttctggatga aaacttcaaa cgatgcttca  1260
gagagttctg tatcccaacc tcttccaaca ttgagcaaca aaactccact cgaattcgtc  1320
agaacactag agaccacccc tccacggcca atacagtgga tagaactaat catcagctag  1380
aaaatctgga agcagaaact gctccgttgc cctaacaggg tctcatgcca ttccgacctt  1440
caccaagctt agaagccacc atgtatgtgg aagcaggttg cttcaagaat gtgtaggagg  1500
ctctaattct ctaggaaagt gcctactttt aggtcatcca acctctttcc tctctggcca  1560
```

-continued

```
ctctgctctg cacattagag ggacagccaa aagtaagtgg agcatttgga aggaaaggaa    1620
tataccacac cgaggagtcc agtttgtgca agacacccag tggaaccaaa acccatcgtg    1680
gtatgtgaat tgaagtcatc ataaaaggtg acccttctgt ctgtaagatt ttattttcaa    1740
gcaaatattt atgacctcaa caaagaagaa ccatcttttg ttaagttcac cgtagtaaca    1800
cataaagtaa atgctacctc tgatcaaagc accttgaatg gaaggtccga gtcttttag     1860 tgtttttgca agggaatgaa tccattattc tattttagac ttttaacttc aacttaaaat    1920
tagcatctgg ctaaggcatc attttcacct ccatttcttg gttttgtatt gtttaaaaaa    1980
aataacatct ctttcatcta gctccataat tgcaagggaa gagattagca tgaaaggtaa    2040
tctgaaacac agtcatgtgt canctgtaga aaggttgatt ctcatgcact ncaaatactt    2100
ccaaagagtc atcatggggg atttttcatt cttaggcttt cagtggtttg ttcctggaat    2160
tc                                                                   2162
```

<210> SEQ ID NO 2
<211> LENGTH: 400
<212> TYPE: PRT
<213> ORGANISM: Homo sapiens

<400> SEQUENCE: 2

```
Met Asp Ser Ser Ala Ala Pro Thr Asn Ala Ser Asn Cys Thr Asp Ala
 1               5                  10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asn Leu Gly Gly Arg Asp Ser Leu Cys Pro Pro Thr Gly Ser
         50                 55                  60

Pro Ser Met Ile Thr Ala Ile Thr Ile Met Ala Leu Tyr Ser Ile Val
 65                 70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
         115                 120                 125

Asn Tyr Leu Met Gly Thr Trp Pro Phe Gly Thr Ile Leu Cys Lys Ile
     130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
     210                 215                 220

His Pro Thr Trp Tyr Trp Glu Asn Leu Val Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
```

```
                    260                  265                  270
Lys Asp Arg Asn Leu Arg Arg Ile Thr Arg Met Val Leu Val Val Val
            275                  280                  285

Ala Val Phe Ile Val Cys Trp Thr Pro Ile His Ile Tyr Val Ile Ile
290                  295                  300

Lys Ala Leu Val Thr Ile Pro Glu Thr Thr Phe Gln Thr Val Ser Trp
305                  310                  315                  320

His Phe Cys Ile Ala Leu Gly Tyr Thr Asn Ser Cys Leu Asn Pro Val
                325                  330                  335

Leu Tyr Ala Phe Leu Asp Glu Asn Phe Lys Arg Cys Phe Arg Glu Phe
            340                  345                  350

Cys Ile Pro Thr Ser Ser Asn Ile Glu Gln Gln Asn Ser Thr Arg Ile
        355                  360                  365

Arg Gln Asn Thr Arg Asp His Pro Ser Thr Ala Asn Thr Val Asp Arg
    370                  375                  380

Thr Asn His Gln Leu Glu Asn Leu Glu Ala Glu Thr Ala Pro Leu Pro
385                  390                  395                  400
```

<210> SEQ ID NO 3
<211> LENGTH: 398
<212> TYPE: PRT
<213> ORGANISM: Rattus norvegicus

<400> SEQUENCE: 3

```
Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Gly Gly Asn Asp Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
            85                  90                  95

Thr Lys Met Lys Thr Ala Thr Asn Ile Tyr Ile Phe Asn Leu Ala Leu
        100                 105                 110

Ala Asp Ala Leu Ala Thr Ser Thr Leu Pro Phe Gln Ser Val Asn Tyr
    115                 120                 125

Leu Met Gly Thr Trp Pro Phe Gly Thr Ile Leu Cys Lys Ile Val Ile
130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
            165                 170                 175

Asp Phe Arg Thr Pro Arg Asn Ala Lys Ile Val Asn Val Cys Asn Trp
        180                 185                 190

Ile Leu Ser Ser Ala Ile Gly Leu Pro Val Met Phe Met Ala Thr Thr
    195                 200                 205

Lys Tyr Arg Gln Gly Ser Ile Asp Cys Thr Leu Thr Phe Ser His Pro
210                 215                 220

Thr Trp Tyr Trp Glu Asn Leu Leu Lys Ile Cys Val Phe Ile Phe Ala
225                 230                 235                 240
```

-continued

```
Phe Ile Met Pro Val Leu Ile Ile Thr Val Cys Tyr Gly Leu Met Ile
                245                 250                 255
Leu Arg Leu Lys Ser Val Arg Met Leu Ser Gly Ser Lys Glu Lys Asp
                260                 265                 270
Arg Asn Leu Arg Arg Ile Thr Arg Met Val Leu Val Val Val Ala Val
                275                 280                 285
Phe Ile Val Cys Trp Thr Pro Ile His Ile Tyr Val Ile Ile Lys Ala
            290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
                340                 345                 350
Pro Thr Ser Ser Thr Ile Glu Gln Gln Asn Ser Thr Arg Val Arg Gln
                355                 360                 365
Asn Thr Arg Glu His Pro Ser Thr Ala Asn Thr Val Asp Arg Thr Asn
            370                 375                 380
His Gln Leu Glu Asn Leu Glu Ala Glu Thr Ala Pro Leu Pro
385                 390                 395

<210> SEQ ID NO 4
<211> LENGTH: 372
<212> TYPE: PRT
<213> ORGANISM: Rattus norvegicus

<400> SEQUENCE: 4

Met Glu Pro Val Pro Ser Ala Arg Ala Glu Leu Gln Phe Ser Leu Leu
  1               5                  10                  15
Ala Asn Val Ser Asp Thr Phe Pro Ser Ala Phe Pro Ser Ala Ser Ala
                 20                  25                  30
Asn Ala Ser Gly Ser Pro Gly Ala Arg Ser Ala Ser Ser Leu Ala Leu
             35                  40                  45
Ala Ile Ala Ile Thr Ala Leu Tyr Ser Ala Val Cys Ala Val Gly Leu
         50                  55                  60
Leu Gly Asn Val Leu Val Met Phe Gly Ile Val Arg Tyr Thr Lys Leu
 65                  70                  75                  80
Lys Thr Ala Thr Asn Ile Tyr Ile Phe Asn Leu Ala Leu Ala Asp Ala
                 85                  90                  95
Leu Ala Thr Ser Thr Leu Pro Phe Gln Ser Ala Lys Tyr Leu Met Glu
                100                 105                 110
Thr Trp Pro Phe Gly Glu Leu Leu Cys Lys Ala Val Leu Ser Ile Asp
            115                 120                 125
Tyr Tyr Asn Met Phe Thr Ser Ile Phe Thr Leu Thr Met Met Ser Val
130                 135                 140
Asp Arg Tyr Ile Ala Val Cys His Pro Val Lys Ala Leu Asp Phe Arg
145                 150                 155                 160
Thr Pro Ala Lys Ala Lys Leu Ile Asn Ile Cys Ile Trp Val Leu Ala
                165                 170                 175
Ser Gly Val Gly Val Pro Ile Met Val Met Ala Val Thr Gln Pro Arg
            180                 185                 190
Asp Gly Ala Val Val Cys Thr Leu Gln Phe Pro Ser Pro Ser Trp Tyr
        195                 200                 205
Trp Asp Thr Val Thr Lys Ile Cys Val Phe Leu Phe Ala Phe Val Val
210                 215                 220
```

```
Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
            245                 250                 255

Arg Arg Ile Thr Arg Met Val Leu Val Val Val Gly Ala Phe Val Val
            260                 265                 270

Cys Trp Ala Pro Ile His Ile Phe Val Ile Val Trp Thr Leu Val Asp
            275                 280                 285

Ile Asn Arg Arg Asp Pro Leu Val Val Ala Ala Leu His Leu Cys Ile
    290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Ala Pro
                325                 330                 335

Cys Gly Gly Gln Glu Pro Gly Ser Leu Arg Arg Pro Arg Gln Ala Thr
            340                 345                 350

Ala Arg Glu Arg Val Thr Ala Cys Thr Pro Ser Asp Gly Pro Gly Gly
            355                 360                 365

Gly Ala Ala Ala
    370

<210> SEQ ID NO 5
<211> LENGTH: 380
<212> TYPE: PRT
<213> ORGANISM: Rattus norvegicus

<400> SEQUENCE: 5

Met Glu Ser Pro Ile Gln Ile Phe Arg Gly Glu Pro Gly Pro Thr Cys
1               5                   10                  15

Ala Pro Ser Ala Cys Leu Leu Pro Asn Ser Ser Ser Trp Phe Pro Asn
            20                  25                  30

Trp Ala Glu Ser Asp Ser Asn Gly Ser Val Gly Ser Glu Asp Gln Gln
        35                  40                  45

Leu Glu Pro Ala His Ile Ser Pro Ala Ile Pro Val Ile Ile Thr Ala
    50                  55                  60

Val Tyr Ser Val Val Phe Val Val Gly Leu Val Gly Asn Ser Leu Val
65                  70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
            100                 105                 110

Pro Phe Gln Ser Ala Val Tyr Leu Met Asn Ser Trp Pro Phe Gly Asp
        115                 120                 125

Val Leu Cys Lys Ile Val Ile Ser Ile Asp Tyr Tyr Asn Met Phe Thr
    130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ala Ser Ser Val Gly Ile Ser
            180                 185                 190

Ala Ile Val Leu Gly Gly Thr Lys Val Arg Glu Asp Val Asp Val Ile
        195                 200                 205

Glu Cys Ser Leu Gln Phe Pro Asp Asp Glu Tyr Ser Trp Trp Asp Leu
```

-continued

```
            210                 215                 220
Phe Met Lys Ile Cys Val Phe Val Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
                260                 265                 270

Thr Lys Leu Val Leu Val Val Val Ala Val Phe Ile Ile Cys Trp Thr
            275                 280                 285

Pro Ile His Ile Phe Ile Leu Val Glu Ala Leu Gly Ser Thr Ser His
            290                 295                 300

Ser Thr Ala Val Leu Ser Ser Tyr Tyr Phe Cys Ile Ala Leu Gly Tyr
305                 310                 315                 320

Thr Asn Ser Ser Leu Asn Pro Val Leu Tyr Ala Phe Leu Asp Glu Asn
                325                 330                 335

Phe Lys Arg Cys Phe Arg Asp Phe Cys Phe Pro Ile Lys Met Arg Met
                340                 345                 350

Glu Arg Gln Ser Thr Asn Arg Val Arg Asn Thr Val Gln Asp Pro Ala
            355                 360                 365

Ser Met Arg Asp Val Gly Gly Met Asn Lys Pro Val
    370                 375                 380
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 6
ttgtcccact tagatggcga cctgtccgac cca                33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 7
accgcatggg tcggacaggt cgccatctaa gtg                33